US006240315B1

(12) United States Patent
Mo et al.

(10) Patent No.: US 6,240,315 B1
(45) Date of Patent: May 29, 2001

(54) ELECTRICAL APPARATUS FOR MEDICAL TREATMENT USING EMG ENVELOPE SIGNAL

(76) Inventors: Seung Kee Mo, #107-703 Kangbyun Apt., Manyun-dong, Seoh-ku, Taejon 302-150; Soo Yeol Lee, #101-1406 Samil Apt., Chilkeum-dong, Choongjoo-shi, Choongcheongbook-do, 380-220, both of (KR)

( * ) Notice: Subject to any disclaimer, the term of this patent is extended or adjusted under 35 U.S.C. 154(b) by 0 days.

(21) Appl. No.: 09/583,197

(22) Filed: May 30, 2000

Related U.S. Application Data

(62) Division of application No. 09/251,390, filed on Feb. 17, 1999.

(30) Foreign Application Priority Data

Feb. 25, 1998 (KR) .................................................... 98-5998
Jul. 21, 1998 (KR) ................................................. 98-29206
Feb. 8, 1999 (KR) .................................................... 99-4237

(51) Int. Cl.[7] ...................................................... A61N 1/00
(52) U.S. Cl. ............................................................. 607/41
(58) Field of Search ................................. 67/40, 41, 138; 128/905; 600/546, 545, 587, 591, 29

(56) References Cited

U.S. PATENT DOCUMENTS

| 4,571,750 | 2/1986 | Barry . |
|---|---|---|
| 4,632,126 | 12/1986 | Aguilar . |
| 4,742,833 | 5/1988 | Barsom . |
| 4,881,526 | * 11/1989 | Johnson et al. ........................ 600/546 |
| 5,103,835 | 4/1992 | Yamada et al. . |
| 5,321,445 | 6/1994 | Fossetti . |
| 5,411,548 | 5/1995 | Carmen . |
| 5,423,329 | 6/1995 | Ergas . |
| 5,465,729 | 11/1995 | Bittman et al. . |

* cited by examiner

*Primary Examiner*—George R. Evanisko
(74) *Attorney, Agent, or Firm*—Sheridan Ross P.C.

(57) ABSTRACT

An apparatus for medical treatment is provided, which can reduce the load of signal processing and allows the patient to recognize the state of his/her muscular contraction more easily. The apparatus for medical treatment being operatively coupled to at least one electrode adapted to be contacted to a body portion or inserted into a body cavity, comprises: an EMG signal processor for performing a signal processing related to an EMG signal and including an envelope detector for receiving the EMG signal originated from the electrodes, and for producing an EMG envelope signal; a display unit for displaying information related to a medical treatment based on the EMG envelope signal; an operation unit; a memory for storing an treatment related data including the training goal waveform information; a stimulation signal generator for generating a stimulation signal; a main controller for controlling the operation of the above elements. Also, a universal connecting member is made in the cable for connecting to an electrode, so that various shape of electrodes are capable of being coupled to the main body of medical treatment apparatus. The compactness of the medical treatment apparatus reduces the cost for manufacturing and the patient is allowed to easily recognize the state of himself (or herself) during biofeedback therapy, thereby making the therapy efficient.

5 Claims, 21 Drawing Sheets

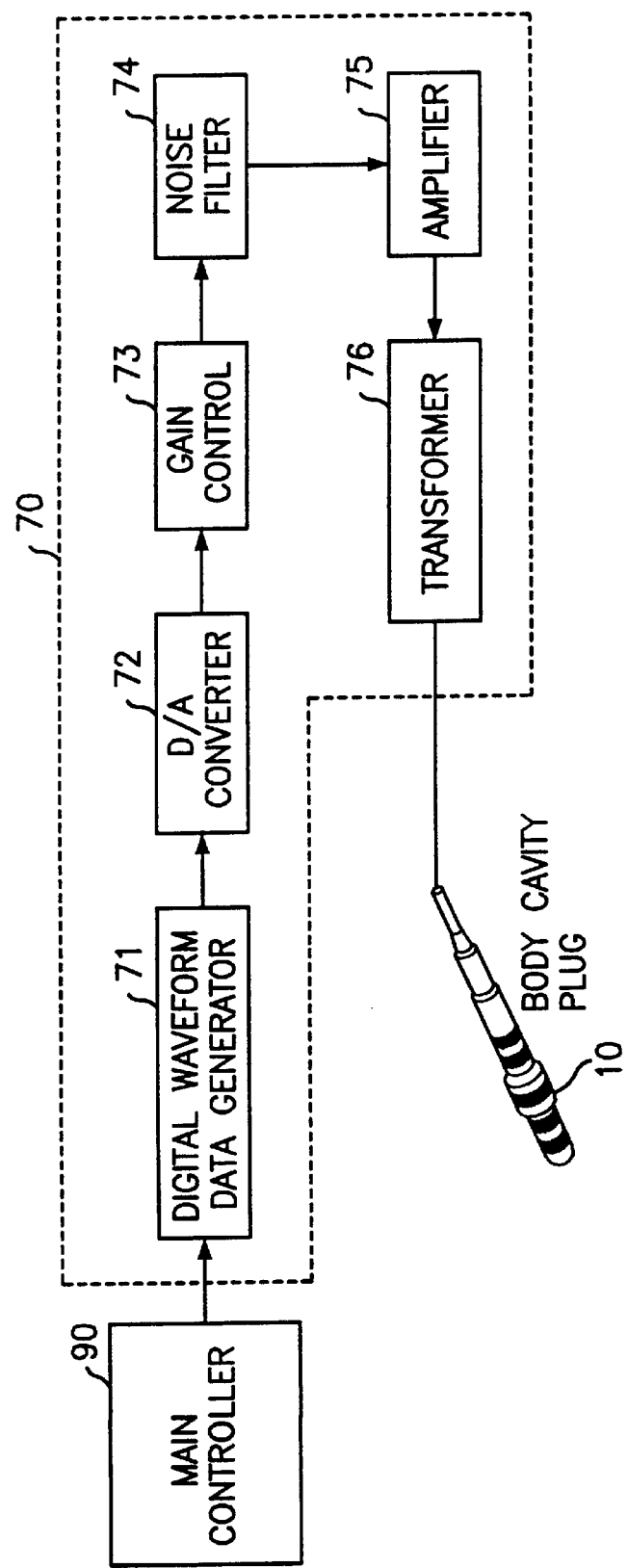

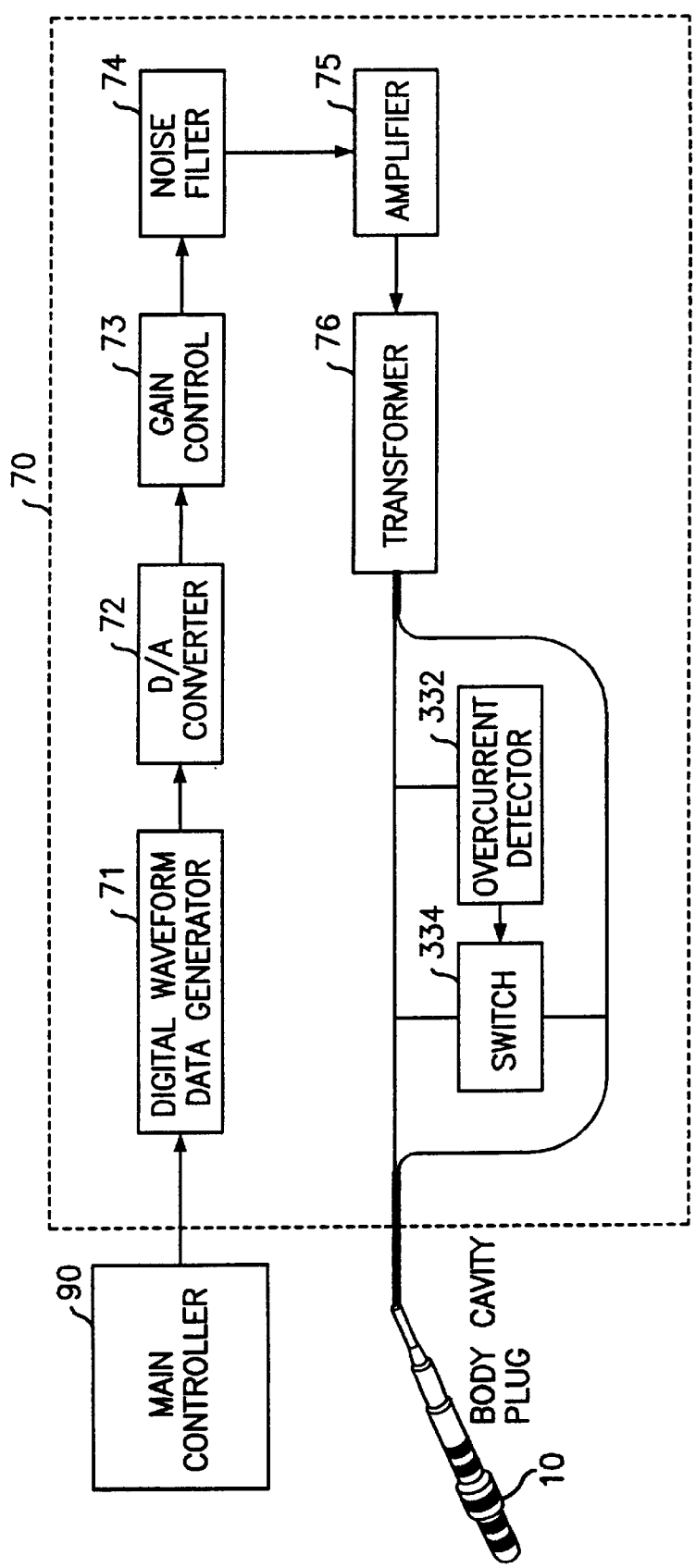

ELECTRICAL APPARATUS FOR MEDICAL TREATMENT USING EMG ENVELOPE SIGNAL

This patent is a division of U.S. patent application Ser. No. 09/251,390 filed on Feb. 17, 1999, which claims foreign priority benefits under 35 U.S.C. §119 from Korean Patent Application Serial No. 1998-5998 filed Feb. 25, 1998, Korean Patent Application Serial No. 1998-29206 filed Jul. 21, 1998, and Korean Patent Application Serial No. 1999-4237 filed Feb. 8, 1999.

BACKGROUND OF THE INVENTION

The present invention relates to an apparatus for electrical therapy for medical purposes, more particularly, to an apparatus for urinary incontinence treatment using an EMG (Electromyography) signal.

Urinary incontinence is a common problem throughout the world and is particularly prevalent in the female population and in the aged. A large number of women suffer from urinary incontinence due to childbirth or general deterioration of body structures as an aging process and so on. It is known that about 20–30% of women over 50 years old suffer from urinary incontinence. Resulting from urinary incontinence is embarrassment, discomfort and distress, loss of sleep and the necessity for large monetary disbursements by the patients for absorbent pads, diapers, rubber sheeting and for cleaning of soiled clothing.

These days the treatment for urinary incontinence includes surgery, physical rehabilitation and drug therapy.

The surgery treatment methods are invasive and thus most patients hesitate to choose this option over others. In addition, the drug therapies are known to provide very limited effectiveness. However, treatment for urinary incontinence is viewed differently by society as many non-invasive and non-pharmaceutical treatment methods are being introduced lately. Among such treatment methods, a biofeedback therapy and a neuromuscular electrical stimulation method are most commonly recognized as major treatment methods. These treatments have been proven very effective, safe to use and relatively inexpensive. In biofeedback therapy, repetitive contractions of pelvic floor muscles improve the strength of the pelvic floor muscles. Neuromuscular electrical stimulation method applies current pulses to pelvic floor muscles so that the motor nerve fibers are electrically stimulated. For more effective treatment for urinary incontinence, it is desirable that both biofeedback and neuromuscular electrical stimulation methods are performed at the same time, rather than one of them being independently performed.

For biofeedback treatment method for urinary incontinence, a patient follows pre-defined training courses to contract her pelvic floor muscles. At this time, it is very important to let the patient know how strong the pelvic floor muscles can contract according to her will.

This is because the effectiveness of the treatment increases along with the patient's positive attitude and willingness by objectively recognizing the improvement of the contractile force as the training progresses. In addition, doctors can create an effective training program in accordance with the observation of the training progress.

EMG signals are measured by the intensity of EMG proportional to the contractile force of the pelvic floor muscles. In doing so, one or more conductive electrodes are contacted with the surface of the vaginal wall. The electrode senses the voltage driven by the muscles, and the frequency of human EMG signals lies in the band between 20 and 800 Hz, which includes higher frequency components than other EMG signals.

FIG. 1 illustrates the typical waveform of such an EMG signal. However, such instantaneous transition of the EMG signals as seen in FIG. 1 is not required for analyzing the contractile force, but important is the overall transition of the amplitude of EMG signals as seen in FIG. 2, namely an envelope signal. Such an envelope of EMG signal has low frequency components, that is below 10 Hz.

However, the sampling frequency needs to be over 1,600 Hz in order to eliminate possible errors due to A/D conversion, because the raw EMG signal data contains high frequency components. However sampling using such a high frequency causes to complicate the structure of the device and raises the manufacturing cost.

In addition, the existing electrical therapy devices, such as urinary incontinence treatment devices, constipation/fecal incontinence treatment devices and low-frequency physical therapy devices, are very similar in their operating principles. Although, it is common to construct separate devices for each treatment purpose because each device has a unique form of electrode.

SUMMARY OF THE INVENTION

Accordingly, the object of the present invention is to provide a less expensive and more effective apparatus for urinary incontinence treatment.

Another object of the present invention is to provide a compact in its structure and portable apparatus for urinary incontinence treatment.

Still Another object of the present invention is to provide an electrical therapy apparatus for medical purposes such as urinary incontinence treatment, constipation/fecal incontinence treatment or low-frequency physical therapy.

Yet another object of the present invention is to provide a urinary incontinence treatment apparatus which lets the patient recognize the state of his/her muscular contraction more easily.

To achieve the above-mentioned objects, the present invention provides a medical treatment apparatus.

According to one aspect of the present invention, an apparatus for medical treatment is operatively coupled to at least one electrode adapted to be contacted to a portion of a body or inserted into a body cavity for sensing an EMG signal therefrom. The apparatus comprises: an envelope detector for receiving the EMG signal captured by the electrodes, and for filtering the EMG signal to produce an EMG envelope signal; and a display unit for displaying an information on medical treatment based on the EMG envelope signal. In one embodiment of the present invention, the apparatus further comprises: a memory for storing treatment-related data including a predefined training goal waveform information, and wherein the display unit displays the information on medical treatment based on the predefined training goal waveform information in addition to the EMG envelope signal. In another embodiment of the present invention, the apparatus may also comprise a main controller for controlling the envelope detector, the memory and the display unit. Here, the display unit may comprise a screen and a display controller coupled to the screen. Also, a first waveform of the EMG envelope signal and a second waveform of the training goal signal are concurrently displayed on the screen during medical treatment for easy comparison. In yet another embodiment of the present invention, the apparatus may also include a memory for storing treatment-related data including the training goal waveform information; and a main controller for controlling the envelope detector, the memory and the display unit, and the display unit includes a screen and a display controller coupled thereto the screen. Also, the apparatus may include an operation unit coupled to the main controller for inputting user's manipulation data to the main controller. The operation unit includes a first setting means for inputting an information related to a stimulation signal waveform to be delivered to the patient's body through the electrode; a second setting means for setting the operational mode of the apparatus. The operational mode of the apparatus may include a stimulation mode for carrying the stimulation signal to the patient's body, a measurement mode for sensing the EMG signal from the patient's body and a combination mode for performing the stimulation and measurement modes alternatively. Here, the operation unit includes a third setting means for selecting either automatic or manual switching between the stimulation and measurement modes, if the combination mode is selected by the second setting means; and a forth setting means for determining the time length from when the stimulation signal is applied to the patient's body to when the switching to the measurement mode is made, if the automatic switching is selected by the third setting means.

According to another aspect of the present invention, provided is an apparatus for medical treatment being operatively coupled to at least one electrode adapted to be contacted to a portion of a body or inserted into a body cavity for sensing EMG signals therefrom, and the apparatus comprises: an EMG signal processor for performing a signal processing related to an EMG signal, including an envelope detector for receiving the EMG signal delivered from the electrodes, and for producing an EMG envelope signal; a display unit for displaying an information related to a medical treatment based on the EMG envelope signal; an operation unit for inputting the user's manipulation data including a training goal waveform information; a memory for storing treatment related data including the training goal waveform information; a stimulation signal generator for generating at least one stimulation signal based on the training goal waveform information which is applied from the operation unit or the memory; and a main controller for controlling the operation of the display unit, the operation unit, the memory, the EMG signal processor and the stimulation signal generator. Here, the EMG signal processor comprises: an amplifier for amplifying the EMG signals delivered from the electrode; a noise filter for eliminating noise included in an output of the amplifier; an envelope detector for detecting an envelope signal from an output of the noise filter and for producing the EMG envelope signal; and an A/D converter for converting an analog form of the EMG envelope signal to a digital form of the EMG envelope signal and applying it to the main controller. In the preferred embodiment, the EMG signal processor further comprises an incorporated EMG signal processor and a separate EMG signal processor. The separate EMG signal processor comprises: a first envelope detector for detecting an envelope from the EMG signal originated from the electrode and for producing a first EMG envelope signal; and a transmitter for transmitting an output of the first envelope detector. Also, the incorporated EMG signal processor comprises: a second envelope detector for detecting an envelope from the EMG signal delivered from the electrode and producing a second EMG envelope signal; a receiver for receiving the first EMG envelope signal transmitted from the transmitter; a channel selector for selecting one between an output of the receiver and an output of the second envelope detector; and an A/D converter for converting an output of the channel selector in an analog form into a digital form thereof and producing it to the main controller. In another preferred embodiment, the EMG signal processor comprises an incorporated EMG signal processor and a separate EMG signal processor. Here, the separate EMG signal processor comprises: a first amplifier for amplifying the EMG signal delivered from the electrode; a first noise filter for removing noise of an output of the first amplifier; a first envelope detector for detecting an envelope from an output of the first noise filter and producing a first EMG signal envelopes; and a transmitter for transmitting an output of the first envelope detector, and the incorporated EMG signal processor comprises: a second amplifier for amplifying the EMG signal delivered from the electrode; a second noise filter for removing noise of an output of the second amplifier; a second envelope detector for detecting an envelope from an output of the second noise filter and producing a second EMG signal envelope; a receiver for receiving the first EMG envelope signal from the transmitter; a channel selector for selecting one between an output of the receiver and an output of the second envelope detector; and an A/D converter for converting an output of the channel selector in an analog form into a digital form thereof and producing it to the main controller. Also, the communication between the transmitter and the receiver may be wireless. In yet another preferred embodiment, the EMG signal processor comprises an incorporated EMG signal processor and a separate EMG signal processor; wherein the separate EMG signal processor comprises: an amplifier for amplifying the EMG signal delivered from the electrode; a noise filter for filtering an output of the amplifier; an envelope detector for detecting an envelope from an output of the noise filter and producing the EMG envelope signal; and a transmitter for transmitting an output of the envelope detector, and wherein the incorporated EMG signal processor comprises: a receiver for receiving the EMG envelope signal from the transmitter; and an A/D converter for converting an output of the receiver in an analog form into a digital form thereof and delivering it to the main controller.

In addition, the apparatus may further comprise a communication processor coupled to the main controller for communicating with an external information device, and an information related to the medical treatment is communicated from the information devices to the memory to be stored, or from the memory to the information devices, using the communication processor. In one preferred embodiment, the stimulation signal generator comprises: a digital waveform data generator for receiving an information on the stimulation signal from the main controller and for generating a digital waveform data based on the information on the stimulation signal; and a D/A converter for converting an output of the digital waveform data generator to an analogue signal. Here, the stimulation signal generator further comprises: an amplifier for amplifying an output of the D/A converter; and a transformer for transforming an output of the amplifier, so as to produce an analog form of the stimulation signal. In another preferred embodiment, the stimulation signal generator further comprises: a switching signal generator for receiving an information related to the stimulating signal and for generating a plurality of switching signals that activates alternately based on the information related to stimulation signal; and a transformer for transforming an output of the waveform generator, so as to produce the stimulating signal in analog form.

In addition, the envelope detector included in the EMG signal processor further comprises: a small-signal full wave rectifier for inputting the EMG signals, and a low-pass filter for filtering an output of the small-signal full-wave rectifier.

According to yet another aspect of the present invention, there is provided an apparatus for medical treatment being operatively coupled to at least one electrode adapted to be contacted to a portion of a body or inserted into a body cavity for sensing an EMG signal therefrom, and the apparatus comprises: an envelope detector for receiving the EMG signal originated from the electrode, and for filtering the EMG signal to produce an EMG envelope signal; an A/D converter for converting the EMG envelope signal in an analog form into a digital form thereof; and a signal processor for processing an information related to a patient's state based on an output of the A/D converter.

According to still further aspect of the present invention, there is provided an apparatus for medical treatment comprising: a main body equipment for generating a stimulation signal to be delivered to a patient's body and processing an EMG signal detected from the patient's body, the main body equipment having at least one port for producing the stimulation signal and for receiving the EMG signal; an interfacing connection part; and a plurality of electrode parts. The interfacing connection part includes a first cable having one end capable of being connected to the port of the main body equipment, and a first type of universal connector formed on the other end of the first cable. Also, each of the plurality of electrode parts comprises at least one electrode adapted to be inserted into a body cavity or to be contacted with a body part, a second cable having one end capable of being connected to the electrodes, and a second type of universal connector on the other end of the first cable to be connected to the first cable. Here, the plurality of electrodes includes an electrode adapted to be inserted into a vagina and/or a pad type electrode. Also, the main body equipment may comprise: an operation unit for selecting at least one of the plurality of electrodes to use; and if the first type of universal connector is coupled to the second type of universal connector, means for determining whether the coupled second type of universal connector complies with an electrode type selected by the operation unit. Alternatively, the main body equipment may comprise: an EMG signal processor including an envelope detector for detecting an envelope from the EMG signal delivered from the electrode and for producing the EMG envelope signal, so as to process the EMG signal; a display unit for displaying information on medical treatment based on the EMG envelope signal; an operation unit for inputting a user's command including an electrode selection command which indicates an electrode to be used; a memory for storing an information related to the medical treatment including a plurality of training goal waveform information each of which corresponds to the plurality of electrodes, respectively; a stimulation signal generator for generating the stimulation signal based on one of the training goal waveform information applied from the memory or the operation unit, so as to apply the stimulation signal to the electrode through the interface connecting parts; and a main controller for controlling the display unit, the operation unit, the memory, the EMG signal processor and the stimulation signal generator.

In short, the EMG signal envelopes have a low frequency, for example below 10 Hz. Sampling frequency must be over 1,600 Hz in order to sample the raw EMG having high frequency components, but in case of sampling EMG signal envelope, the sampling frequency can be lowered to about 20 Hz. Namely, utilization of the envelope information can reduce the sampling frequency by 1/800 and compress the size of the treatment device so that portable urinary incontinence treatment devices could be manufactured easily. Also, another advantage lies in that the present invention can be used not only for urinary incontinence treatment, but also for constipation/fecal incontinence treatment and low-frequency physical therapy, since the cable connecting between the main body equipment and electrodes is divided into two parts with a universal connector in the middle of connecting part, the main body equipment can deliver various stimulation signal waveforms.

BRIEF DESCRIPTION OF THE DRAWINGS

For a more complete understanding of the present invention and the advantage thereof, a reference is now made to the following description taken in conjunction with the accompanying drawings in which:

FIG. 12a to FIG. 12f are detailed block diagrams for illustrating preferred embodiments of the stimulation signal generator 70 shown in FIG. 11;

DETAILED DESCRIPTION OF THE PRESENT INVENTION

Hereafter explained in details is the invention referring to the attached diagrams.

The present invention relates to an electrical apparatus for medical treatment using an EMG signal or EMG signals, in particular for treatment of urinary incontinence and constipation/fecal incontinence and for low-frequency physical therapy. In addition, the apparatus for medical treatment of the present invention includes electrodes for detecting at least one EMG signal from the patient's body part where the treatment is applied or for delivering at least one electrical stimulation signal to the patient's body part to which the treatment is applied. Such electrodes can be tubular (or rod-shaped) for insertion into a body cavity to which the treatment is applied or adhesive pad-type for adhering to the patient's body part to which the treatment is applied.

Hereafter for the convenience of explanation, a urinary incontinence treatment apparatus will be described as an example. However, those skilled in the art will appreciate that the present invention is not limited to the urinary incontinence treatment apparatus, but applied to other medical treatment apparatuses.

Figure 1:
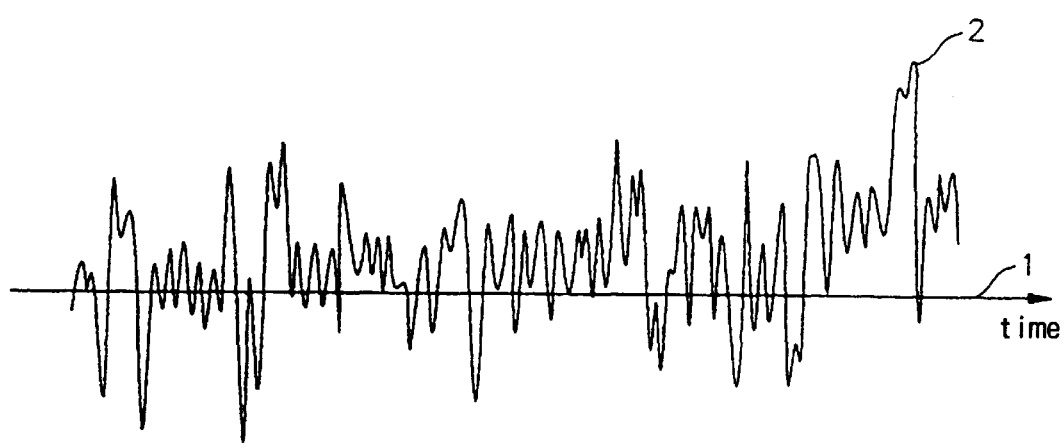
FIG. 1 is an exemplary waveform of an EMG signal in the raw state.
Figure 2:
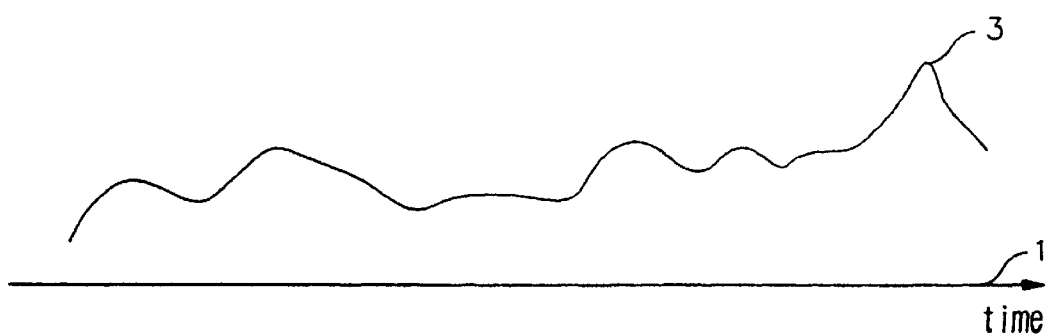
FIG. 2 is an exemplary waveform of an EMG signal envelope.

FIG. 1 is an exemplary waveform of a raw EMG signal detected from the patient's muscle to which the treatment is applied and FIG. 2 is an exemplary waveform of an envelope of the EMG signal in FIG. 1.

As described above, an analysis of envelope information, that is, information on the amplitude of an EMG signal as shown in FIG. 2, is needed for treatment of urinary incontinence instead of the analysis of instantaneous changes of an EMG signal.

As shown in FIG. 2, an envelope of EMG signals has a much lower frequency and most of the energy is concentrated in the band below 10 Hz. Also, the sampling frequency must be over 1,600 Hz in order to sample a raw state of EMG signal, but in case of sampling of the EMG signal envelope, the sampling frequency can be reduced to about 20 Hz. Thus utilization of the envelope information can reduce the sampling frequency by 1/800 and compress the size of the treatment device so that portable urinary incontinence treatment devices could be manufactured easily.

Figure 3:
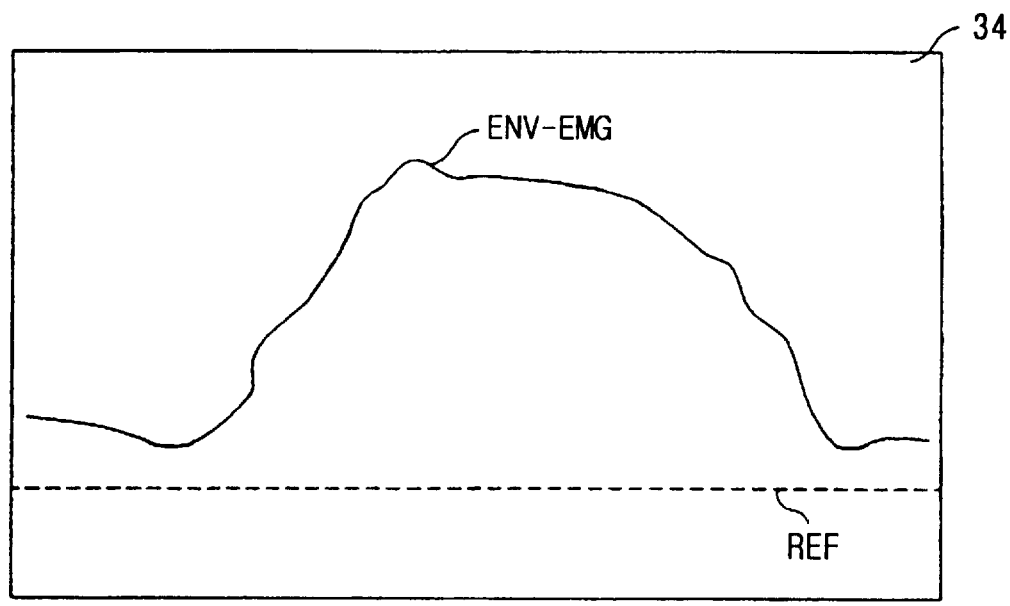
FIG. 3 shows the displayed state in the display screen according to one embodiment of the present invention.

FIG. 3 shows the displayed state of the display screen according to one preferred embodiment of the present invention.

As shown in FIG. 3, an EMG signal envelope ENV-EMG is displayed on the display screen 34 instead of the raw EMG signal as shown in FIG. 1, thus making it easy for the patient and the doctor to recognize the muscle contraction status.

Figure 4:
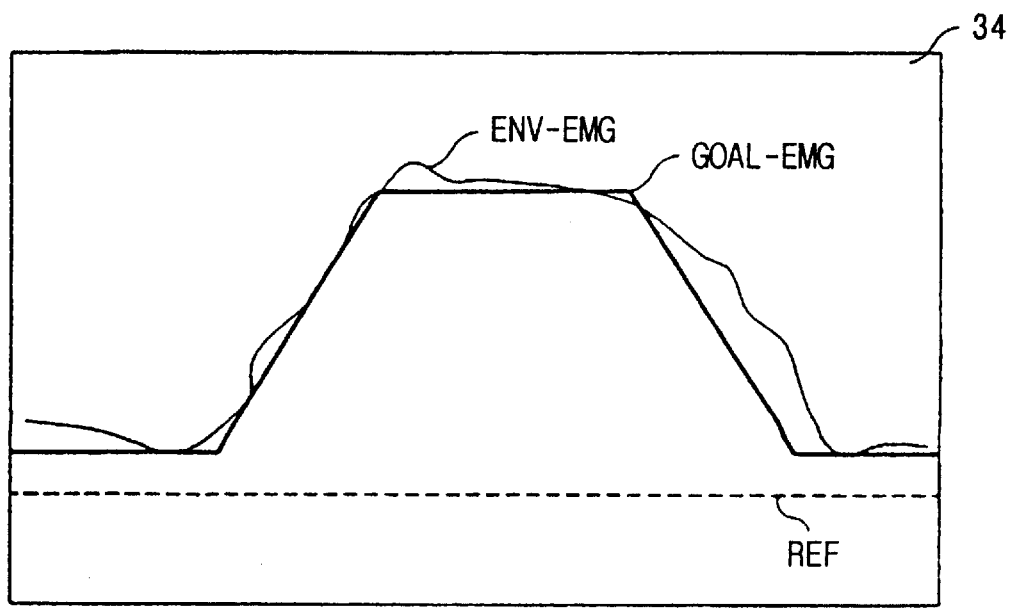
FIG. 4 shows the displayed state of the display screen according to another embodiment of the present invention.

FIG. 4 illustrates the displayed state of the screen according to another preferred embodiment of the present invention.

Referring to FIG. 4, differently from FIG. 3, a treatment goal waveform GOAL-EMG is also displayed along with the EMG signal envelope ENV-EMG on the display screen 34, thus letting the patient recognize the progress of his/her training objectively. Thus an advantage lies in that the patient can be led to contract the muscles following desirable patterns, resulting in the increased effectiveness of the treatment.

Figure 5:
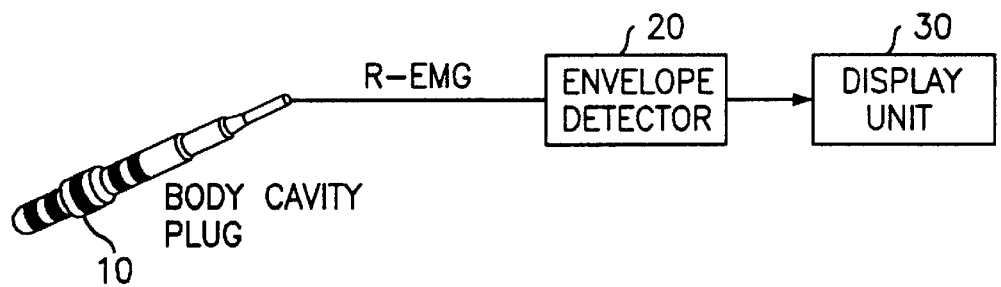
FIG. 5 illustrates the structure of the electrical therapy device according to one embodiment of the present invention.

FIG. 5 shows the configuration of a urinary incontinence treatment apparatus, according to one preferred embodiment of the present invention.

Referring to FIG. 5, the urinary incontinence treatment apparatus comprises an electrode 10 for insertion into a body cavity, an envelope detector 20 and display unit 30. During treatment, the electrode 10 may be inserted into a vagina and contacted to the muscles for detecting EMG from the muscles. The detected EMG signal R-EMG is applied to the envelope detector 20. Then, the raw EMG signal in FIG. 1 is converted into an EMG envelope signal in FIG. 2. This EMG envelope signal is applied to the display unit 30 to be displayed as shown in FIG. 3.

Figure 6:
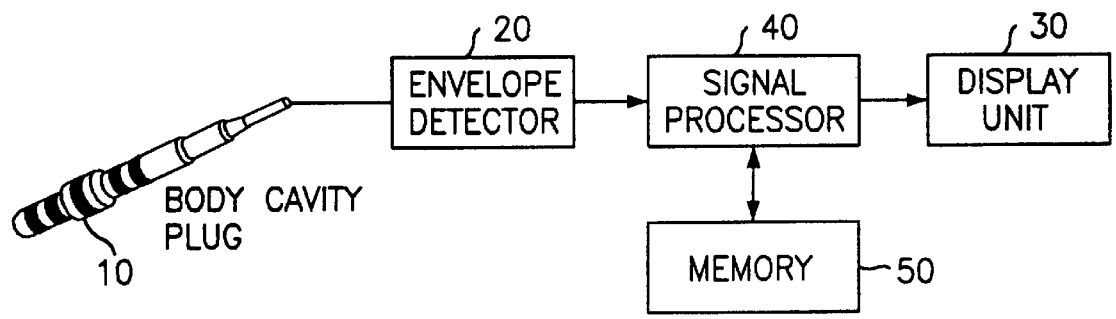
FIG. 6 illustrates the structure of the electrical therapy device according to another embodiment of the present invention.

FIG. 6 shows the configuration of the urinary incontinence treatment apparatus, which comprises an electrode 10 for insertion into a body cavity, an envelope detector 20, a signal processor 40, a memory 50 and display unit 30. In FIG. 6, the same elements as those of FIG. 5 have the same reference numerals attached, and the description thereof will be omitted.

Referring to FIG. 6, the EMG envelope signal produced from the envelope detector 20 is applied to the signal processor 40. The signal processor 40 is coupled to the memory 50 where the information on the training goal waveform GOAL-EMG is stored. The information on the training goal waveform GOAL-EMG, for example, may be the data regarding the desirable intensity and time of contraction of the patient's pelvic floor muscles during treatment. The signal processor 40 analyzes the EMG envelope signals applied from the envelope detector 20, reads the data of the training goal waveform GOAL-EMG from the memory 50, and produces the data related to the EMG envelope signal and the training goal waveform to the display unit 30. In addition, the signal processor 40 can store the result of analysis of the EMG envelope signal in the memory 50, if necessary, which can be used later for analyzing the training history of the patient.

Figure 7:
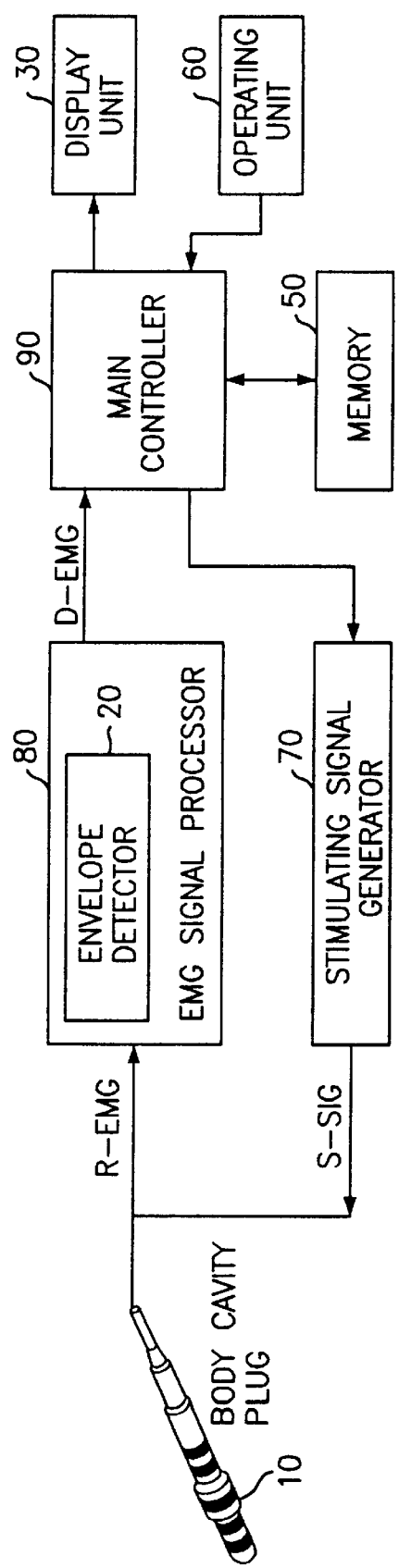
FIG. 7 illustrates the structure of the electrical therapy device according to yet another embodiment of the present invention.

FIG. 7 shows the configuration of the apparatus for medical treatment according to yet another embodiment of the present invention. The apparatus comprises an electrode 10 for insertion into a body cavity, an EMG signal processor 80, a stimulation signal generator 70, a main controller 90, a memory 50, a display unit 30, and an operation unit 60. In FIG. 7, the same elements as those in FIGS. 5 and 6 have the same reference numerals and the description thereof will be omitted.

Referring to FIG. 7, the EMG signal processor 80 including the envelope detector 20 converts the raw EMG signal R-EMG into the EMG envelope signal. If necessary, the EMG signal processor 80 also converts the analog form of the EMG envelope signal to a digital form of the EMG envelope signal D-EMG, so as to apply the digital form of the EMG envelope signal D-EMG to the main controller 90. The main controller 90 analyzes the EMG envelope signal from the EMG signal processor 80, and converts the resulting data of the analysis and the data on the training goal waveforms from the memory 50 into those suitable for displaying, so as to produce them to the display unit 30. Such a controller can be generally implemented by a microprocessor. User can select the operation mode of the urinary incontinence treatment apparatus through the operation unit 60. In more detail, a measurement mode may be set for measuring at least one EMG signal from the vaginal wall muscles using an electrode 10 for insertion into a body cavity, and a stimulation mode may be set for applying at least one electrical stimulation signal S-SIG to the vaginal wall muscles using an electrode 10 for insertion into a body cavity. In addition, a combination mode may be set for applying an electrical stimulation signal S-SIG to the vaginal wall muscles and then measuring EMG signal from the vaginal wall muscles using an electrode 10 for insertion into a body cavity. Namely, the combination mode carries out the stimulation mode and the measurement mode alternately. In the combination mode, the operation unit 60 lets the user to determine whether automatic or manual switching between stimulation and measurement modes may be set. Also, if the automatic switching be selected, the user can set the switching interval of operation from the stimulation and measurement modes.

According to one preferred embodiment of the present invention, the selected form of stimulation signal is applied to the vaginal wall muscles through an electrode 10 for insertion into a body cavity whenever a user presses a specific button. In this case, the button of the operation unit 60 is formed such that it can be easily held or pressed by the user.

In the combination mode, the patient carries out urinary incontinence treatment by electrical stimulation (stimulation mode) and EMG biofeedback (measurement mode), and he/she needs to contract the pelvic floor muscles so that the EMG envelope signal and the training goal waveform GOAL-EMG are best matched on the display unit 30.

The user can also adjust the form of electrical stimulation being applied to the vaginal wall muscles through the electrode 10 for insertion into a body cavity, for example, the waveform type, the intensity and the frequency of the stimulation signal S-SIG. Available waveforms for stimulation signal S-SIG include various pulse waveform and sinusoidal waveform. In addition, various forms of the sinusoidal wave also include full wave, half wave and so on. Also the stimulation signal can either be a current pulse or a voltage pulse.

Different commands by the user are delivered through the operation unit 60 to the main controller 90. The data on the stimulation signal waveform among command signals can be stored in the memory 50 if necessary. This eliminates the inconvenience of the user's having to input the data on the stimulation signals each time he/she carries out the treatment.

The stimulation signal generator 70 generates electrical stimulation signal to be delivered to the muscles through an electrode 10 for insertion into a body cavity under the control of the main controller 90. At this time, the main controller 90, converts the data on the stimulation signals applied from the operation unit 60 or the data on the stimulation signals stored in the memory 50 into appropriate form for the stimulation signal generator 70 so as to produce them and deliver to the stimulation signal generator 70, and activates the signal generator 70 depending on the selected operation mode.

Figure 8:
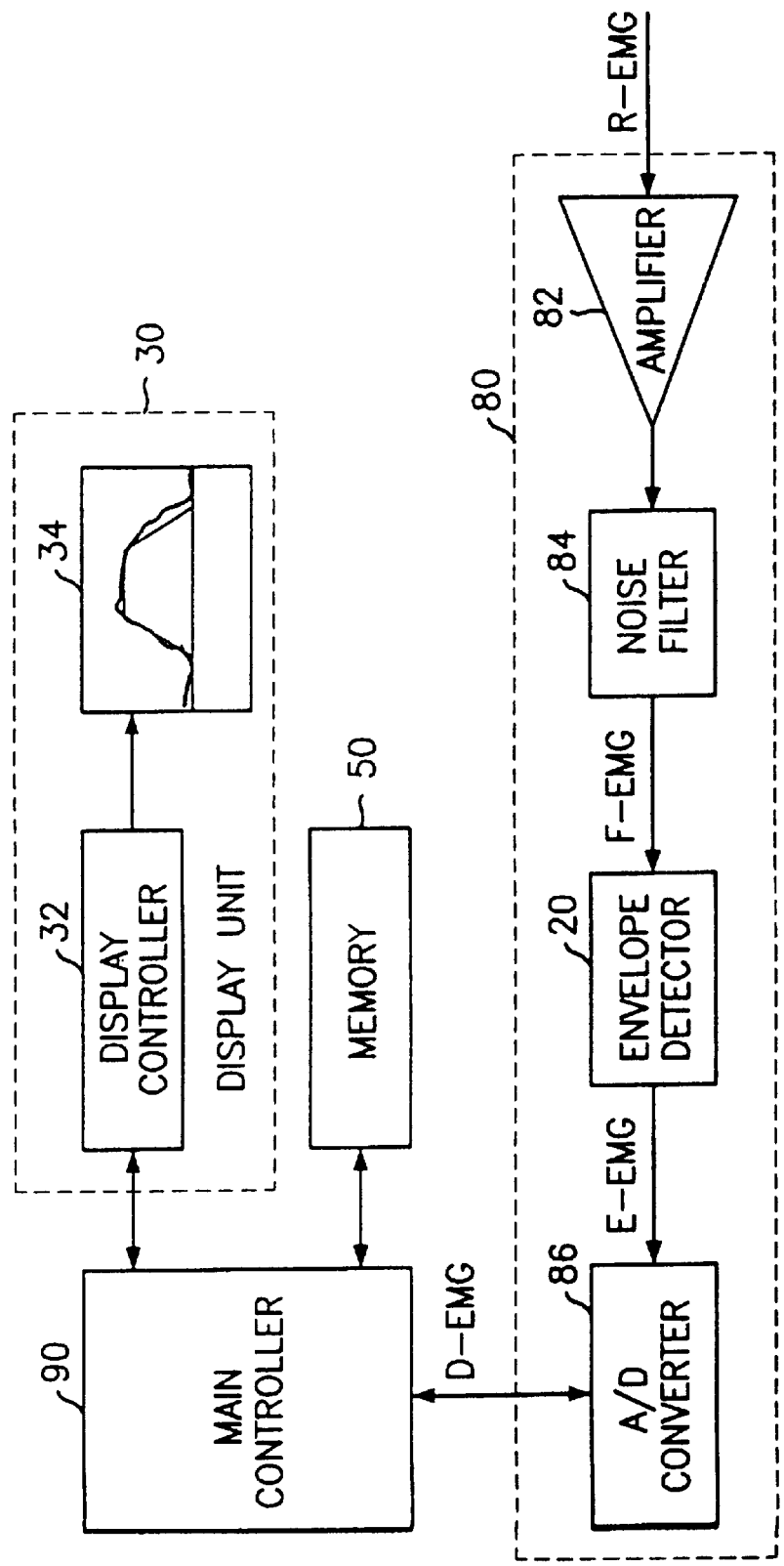
FIG. 8 is a detailed block diagram for illustrating one embodiment of the display unit 30 and the EMG signal processor 80 shown in FIG. 7.

FIG. 8 is a detailed block diagram for illustrating one preferred embodiment of the display unit 30 and the EMG signal processor 80 shown in FIG. 7.

Referring to FIG. 8, the EMG signal processor 80 comprises an analog-to-digital converter(hereinafter called as A/D converter) 86, an envelope detector 20, a noise filter 84 and an amplifier 82, and the display unit 30 comprises a display controller 32 and a screen 34.

The EMG signals detected by the electrode 10, because generally they are too weak in general, are applied to the amplifier 82 to be amplified. The amplifier 82 can be implemented using a differential amplifier, and a reference-potential generator, which is not shown in this figure, may be further included and coupled to the amplifier 82. In this case, the inputs of the differential amplifier and the output of the reference-potential generator could be coupled to the plurality of bands on the electrode 10, respectively.

The output of the amplifier 82 is applied to the noise filter 84 to be filtered. The noise filter 84 can substantially be a band-pass filter. In this case, it is desirable to have the bandwidth of the noise filter 84 to be 20–800 Hz. The output from the noise filter 84 is applied to the envelope detector 20. According to the preferred embodiment of the present invention, the envelope detector 20 may include a low-pass filter. Also, the amplifier 82 and the noise filter 84 can be generally implemented using one or more operational amplifiers.

The envelope detector 20 converts EMG signal as shown in FIG. 1 to EMG envelope signal as shown in FIG. 2. The output from the envelope detector 20 is applied to the A/D converter 86 and converted to EMG envelope signal in a digital form, and then applied to the main controller 90.

In addition, the display controller 32 of the display unit 30 receives the data to be displayed from the main controller 90. The display data include the data for EMG envelope signal, training goal waveform GOAL-EMG and so on. The display controller 32 performs a control required for displaying these data on the screen 34. Thus the screen displays the EMG envelope signal ENV-EMG alone or displays the EMG envelope signal ENV-EMG along with the training goal waveform GOAL-EMG in respect to the reference line as shown in FIG. 4. If necessary, it is possible to send data related to the current operation mode from the main controller 90 to the display controller 32 and display the current operation mode at a predetermined position on the screen 34. Here, because the screen 34 displays the EMG envelope signal as shown in FIG. 2 instead of a raw EMG signal as shown in FIG. 1, it can be implemented with a low resolution. For example, the display unit 30 including the screen 34 can be made with a cost-effective LCD panel of low power-consumption and low resolution. Moreover, it can be made with LED's.

In addition, in case of displaying the training goal waveform GOAL-EMG along with the EMG envelope signal ENV-EMG on screen 34 as shown in FIG. 4, the patient should try to control her pelvic floor muscle to best match the EMG envelope waveform with the training goal waveform.

Figure 9:
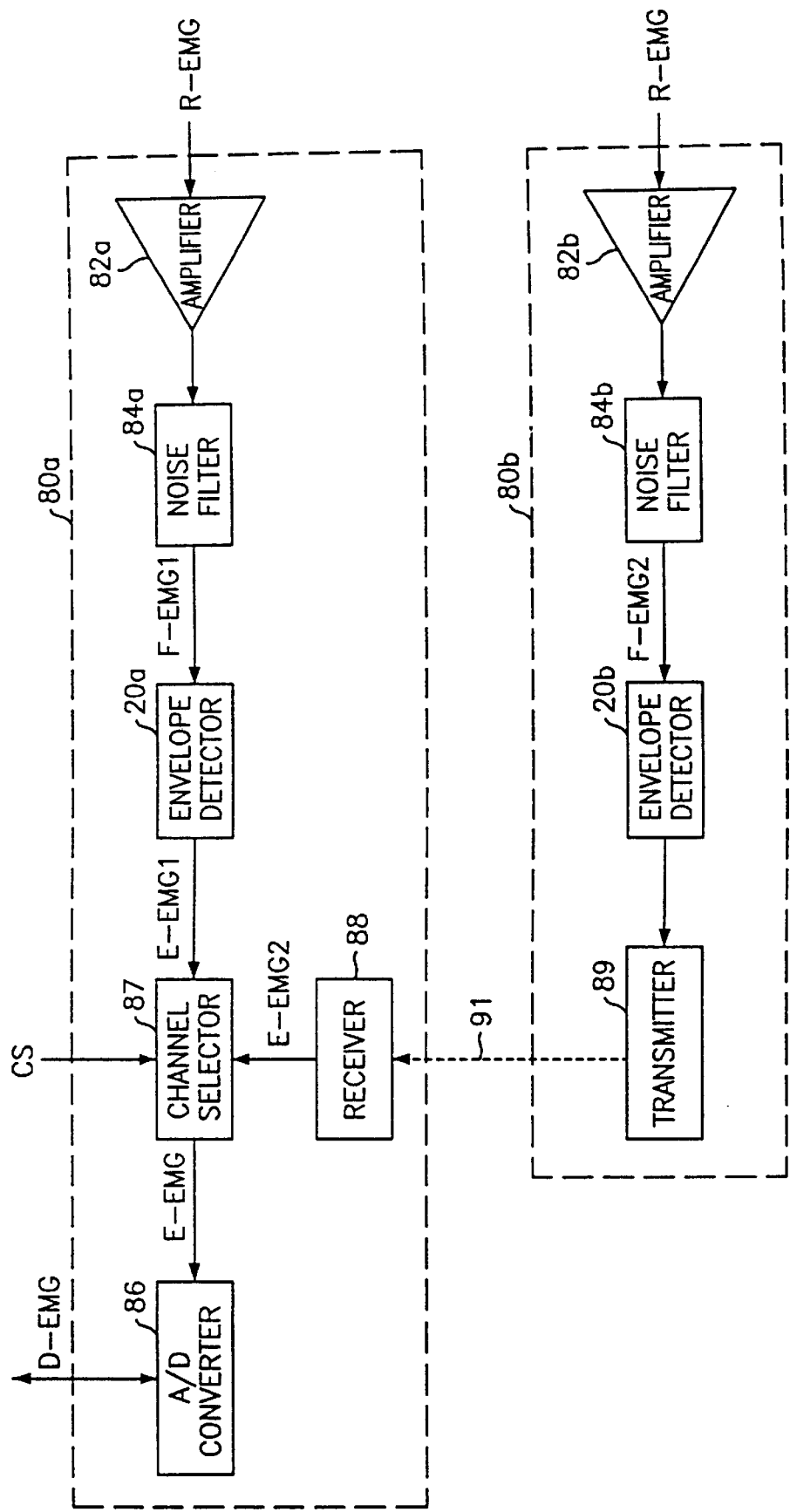
FIG. 9 is a detailed block diagram for illustrating another embodiment of the EMG signal processor 80 shown in FIG. 7.

FIG. 9 is a block diagram of another embodiment of the EMG signal processor 80 in FIG. 7, which comprises an incorporated EMG signal processor 80*a* and a separate EMG signal processor 80*b*.

In FIG. 7, the incorporated EMG signal processor 80*a* can be made into one body(hereinafter called "main body equipment") along with the main controller 90, the memory 50, the display unit 30, the operation unit 60 and the stimulation signal generator 70, and may include an amplifier 82*a*, a noise filter 84*a*, an envelope detector 20*a*, an A/D converter 86, a receiver 88 and a channel selector 87. In the incorporated EMG signal processor 80*a*, the detected EMG signal R-EMG through the electrode 10 is amplified by the amplifier 82*a* and filtered by the noise filter 84*a*. From the output F-EMG1 of the noise filter 84*a*, an EMG envelope signal E-EMG1 is detected by the envelope detector 20*a* and then applied to the channel selector 87.

The separate EMG signal processor 80*b* can be separately made from the main body equipment and includes an amplifier 82*b*, a noise filter 84*b*, an envelope detector 20*b* and a transmitter 89. In the separate EMG signal processor 80*b*, the amplifier 82*b*, the noise filter 84*b* and the envelope detector 20*b* performs the same functions with the amplifier 82*a*, the noise filter 84*a* and the envelope detector 20*a* of the incorporate EMG signal processor 80*a*, respectively. The output of the envelope detector 20*b* in the separate EMG signal processor 80*b* is preferably wirelessly transmitted through the transmitter 89. The EMG signal envelope transmitted through the transmitter 91 is received by an receiver 88 and then applied to the channel selector 87. The channel selector 87 selects one between the EMG envelope signal E-EMG1 from the envelope detector 20a and the EMG envelope signal E-EMG2 originated from the envelope detector 20b, based on a channel selection signal CS, so as to apply the selected EMG envelope signal E-EMG to the A/D converter 86.

Here, the channel selection signal CS can be applied from the main controller 90. In more detail, a user can select the channel through the operational unit 80 of FIG. 7 and the main controller 90 applies the channel selection signal in accordance with the user's selection, to the channel selector 87. In this case, if necessary, the channel selecting information may be stored in the memory 50 so that the same channel may be selected as the previous channel unless the user changes the channel. Also, if the user does not select a channel, the default value stored within the equipment is used for the channel selection signal.

According to another embodiment, the channel selector 87 can be omitted and it is possible to wired-OR operate the output of the envelope detector 20a and that of the receiver 88, so as to apply the wired-OR value to the A/D converter 86.

Also, in the embodiment shown in FIG. 9, the incorporate EMG signal processor 80a and the separate EMG signal processor 80b are selectively coupled to the electrode 10 through a cable.

This separate EMG signal processor 80b can be made portable to be worn by the patient, for example, on a belt. Thus during treatment for urinary incontinence, the patient can insert the electrode 10 into her vagina and put on the separate EMG signal processor 80b, which enables the patient to do light walking or working. As shown in the figure, the separate EMG signal processor 80b is very simple in its structure and can be made in a compact size. Thus it enables the patient to conveniently do light walking or other everyday working during treatment.

Figure 10:
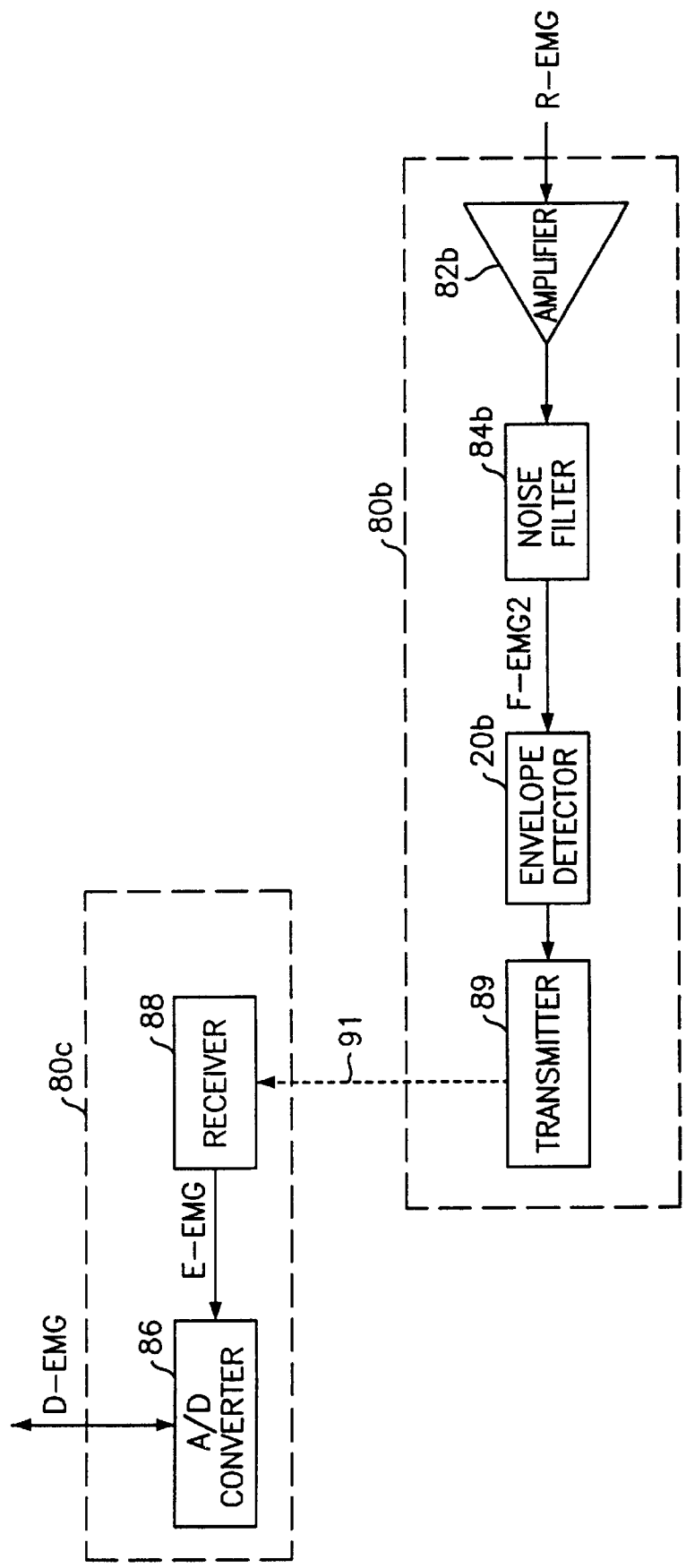
FIG. 10 is a detailed block diagram for illustrating yet another embodiment of the EMG signal processor 80 shown in FIG. 7.

FIG. 10 is a block diagram of yet another embodiment of the EMG signal processor 80 shown in FIG. 7. In this figure, the same parts with those of FIG. 9 have the same reference numerals and the explanation thereof will be omitted.

Referring to FIG. 10, the incorporated EMG signal processor 80c includes an A/D converter 86 and a receiver 88. The receiver 88 receives EMG envelope signals through a wireless transmission line 91 and then applies its output E-EMG to the A/D converter 86. The A/D converter 86 performs an analog-to-digital converting on the E-EMG, so as to apply the digital form of the EMG envelope signal D-EMG to the main controller 90.

Figure 11:
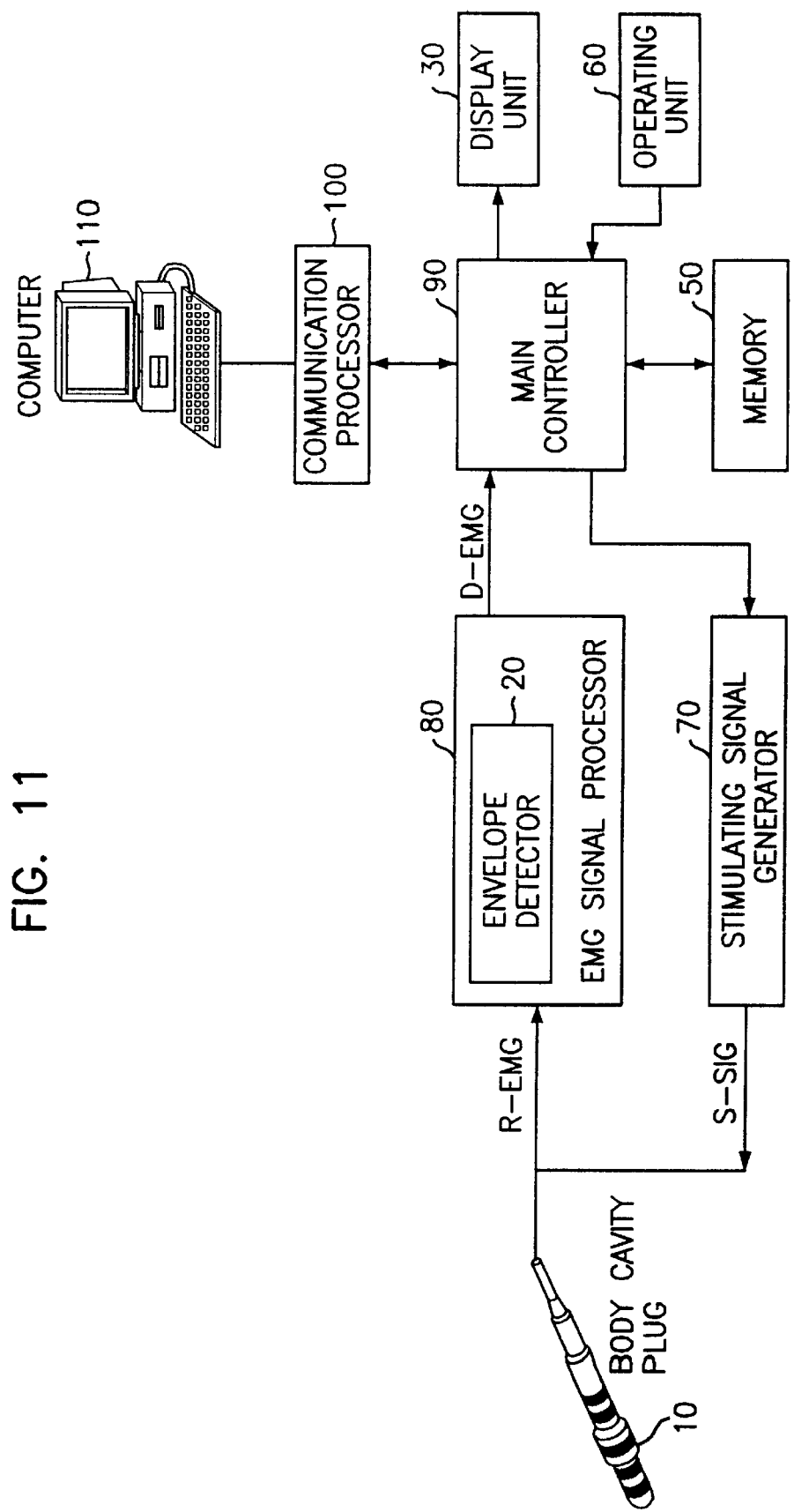
FIG. 11 illustrates the structure of the electrical therapy device according to yet another embodiment of the present invention.

FIG. 11 is a block diagram for illustrating the configuration of the electrical apparatus for medical treatment according to still another preferred embodiment of the present invention, where the urinary incontinence treatment apparatus further comprises a communication processor 100.

Referring to FIG. 11, the communication processor 100 can be coupled to a computer 110 either through a cable or wirelessly.

For treating urinary incontinence, the patient needs to see her doctor periodically, and modify the training goal waveform(s) GOAL-EMG according to the doctor's prescription. In addition, it is required that the patient can carry out the medical treatment for herself (or himself) and store the data generated from the treatment in the memory 50 and then notify the doctor of the data when visiting the hospital.

More concretely, when the patient visits the hospital for consulting with the doctor, the communication processor 100 in the patient's device is coupled through a cable to the computer 110 located in the hospital, and the data on the patient's treatment are communicated between the patient's treatment apparatus and the doctor's computer. The communication processor 100 performs the signal-processing regarding the communication between the treatment apparatus and the computer 110.

FIG. 12 is a detailed block diagram of one preferred embodiment of the stimulation signal generator 70 in FIGS. 7 and 11, where the stimulation signal generator 70 comprises a digital waveform data generator 71, a D/A converter 72, a gain controller 73, a noise filter 74, an amplifier 75 and a transformer 76.

Referring to FIG. 12, the data regarding the stimulation signal S-SIG selected by the user is delivered from the main controller 90 to the digital waveform data generator 71. The digital waveform data generator 71 generates digital waveform data corresponding to the stimulation signal wave form S-SIG. The digital waveform data are converted into an analogue signal in the D/A converter 72, and delivered to the gain controller 73, then the level of the analogue signal is adjusted by the gain controller 73. The stimulation signal is applied to the noise filter 74 so as to be filtered, and then amplified by the amplifier 75. At this time, the amplifier 75 can be usually implemented with at least one operational amplifier. The output from the amplifier 75 is applied to the transformer 76 and amplified again. Here, the output voltage of the transformer 76 is about 300 V peak to peak. At this time, the output level of the transformer 76 can be varied depending on the treatment object. As the transformer, it is preferable that an isolation transformer is used. In addition, the output stimulation signal from the isolation transformer may include mono-phasic, bi-phasic, sinusoidal and semi-sinusoidal signals.

The stimulation signal generator 70 shown in FIG. 12a is especially suitable for non-portable treatment apparatus which may be in general applied for hospital use.

Figure 12B:
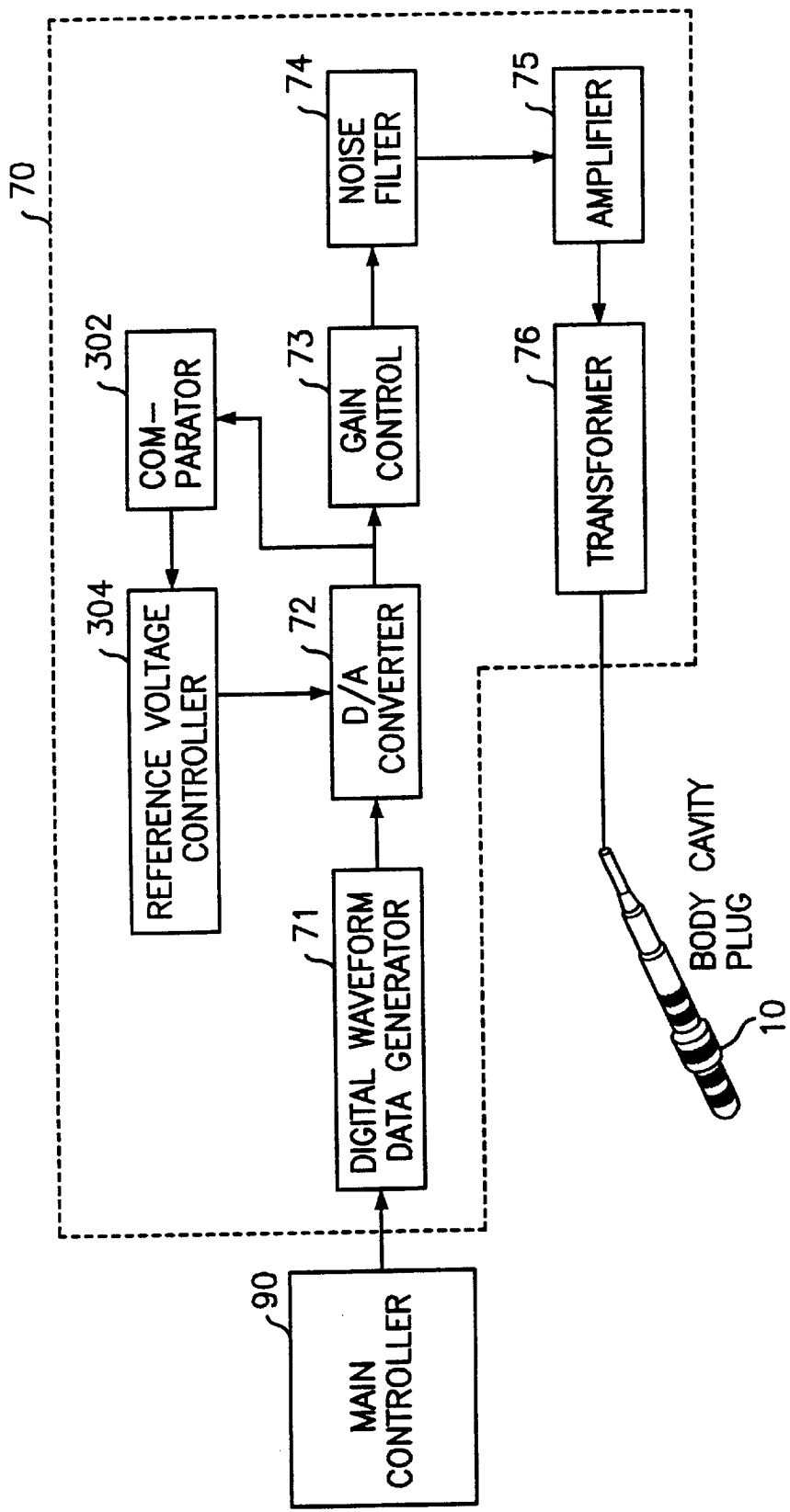

FIG. 12b to FIG. 12e illustrate in detail the stimulation signal generator 70 including the safety circuit. In FIG. 12b, the same parts with those of FIG. 12a have the same reference numerals and the explanation thereof will be omitted.

Referring to FIG. 12b, the stimulation signal generator 70 is a safety circuit consisting of a comparator 302 and a reference voltage controller 304. The comparator 302 receives the output of the D/A converter 72 and then compares so as to see if the output of the D/A converter 72 is equal to or greater than a predetermined voltage. That is, it detects that the output of the D/A converter 72 is too high, so as to generate a reference voltage control signal. The reference voltage controller 304 controls the reference voltage applied to the D/A converter 72 in response to the reference voltage control signal. The D/A converter 72 divides the reference voltage proportionally according to the input data, so as to produce the divided voltage. Thus by controlling the reference voltage, the maximum output of the D/A converter 72 can be controlled. The output of the D/A is applied through the gain control 73, noise filter 74, amplifier 75, and transformer 76 to the body-cavity plug. Therefore, by limiting the output of the D/A converter 72 to a predetermined value, delivering too high of a stimulation signal to a human body though the body-cavity plug 10 can be prevented.

Figure 12C:
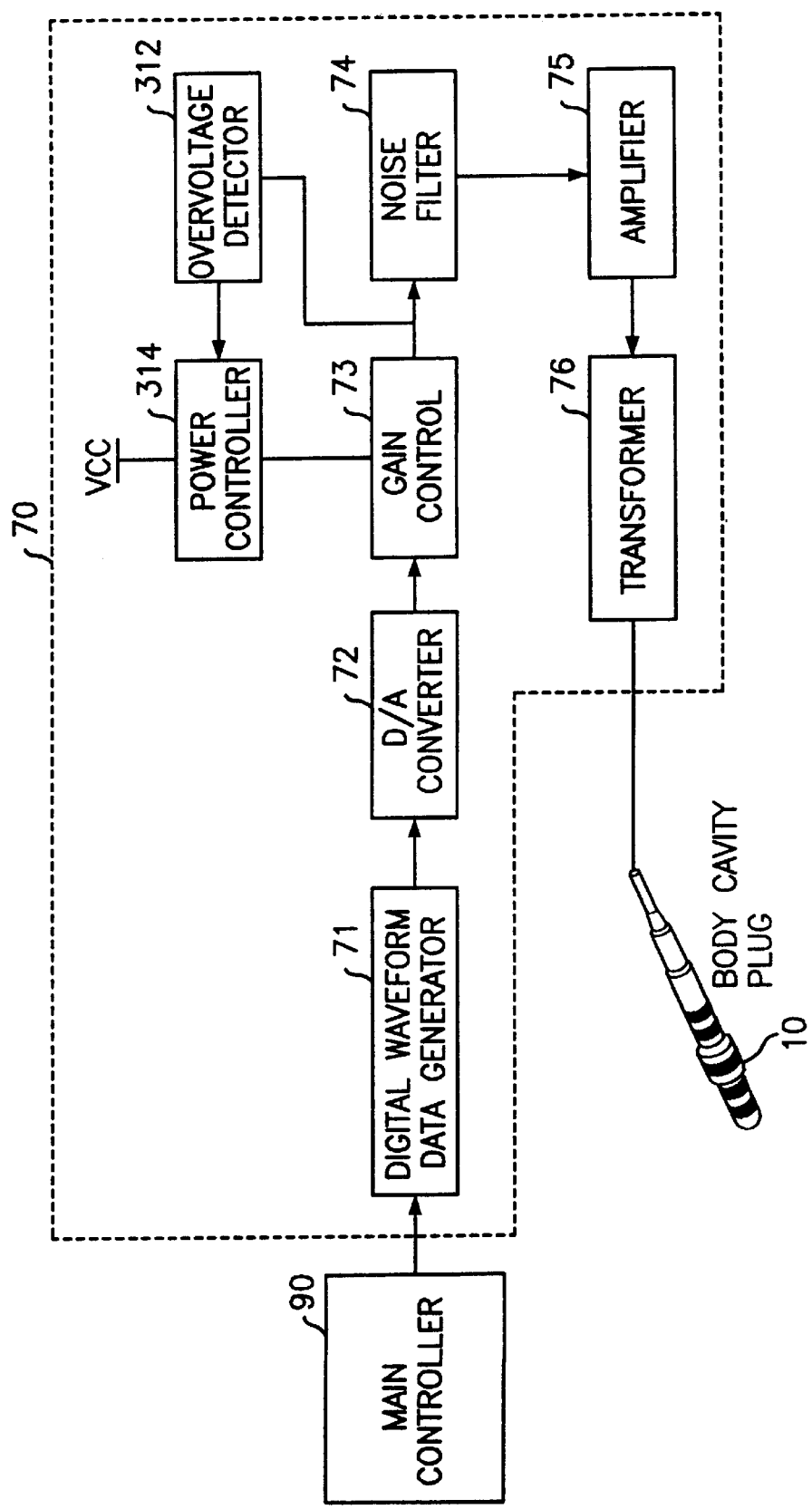

Referring to FIG. 12c, the safety circuit includes an over-voltage detector 312 coupled to the output of the gain control 73 and a power controller (or power breaker) 314. In FIG. 12c, the same parts with those of FIG. 12a have the same reference numerals and the explanation thereof will be omitted.

The over-voltage detector 312 detects that the output of the gain control 73 is greater than a predetermined voltage, so as to generate a power-breaking signal, and can substantially do it by using a comparator. The power controller 314 shuts off the power as a response to the power-breaking signal applied from the over-voltage detector 312. Thus the gain control 73 stops operating and as a result, the stimulation signal delivered to the body-cavity plug 10 is blocked.

Figure 12D:
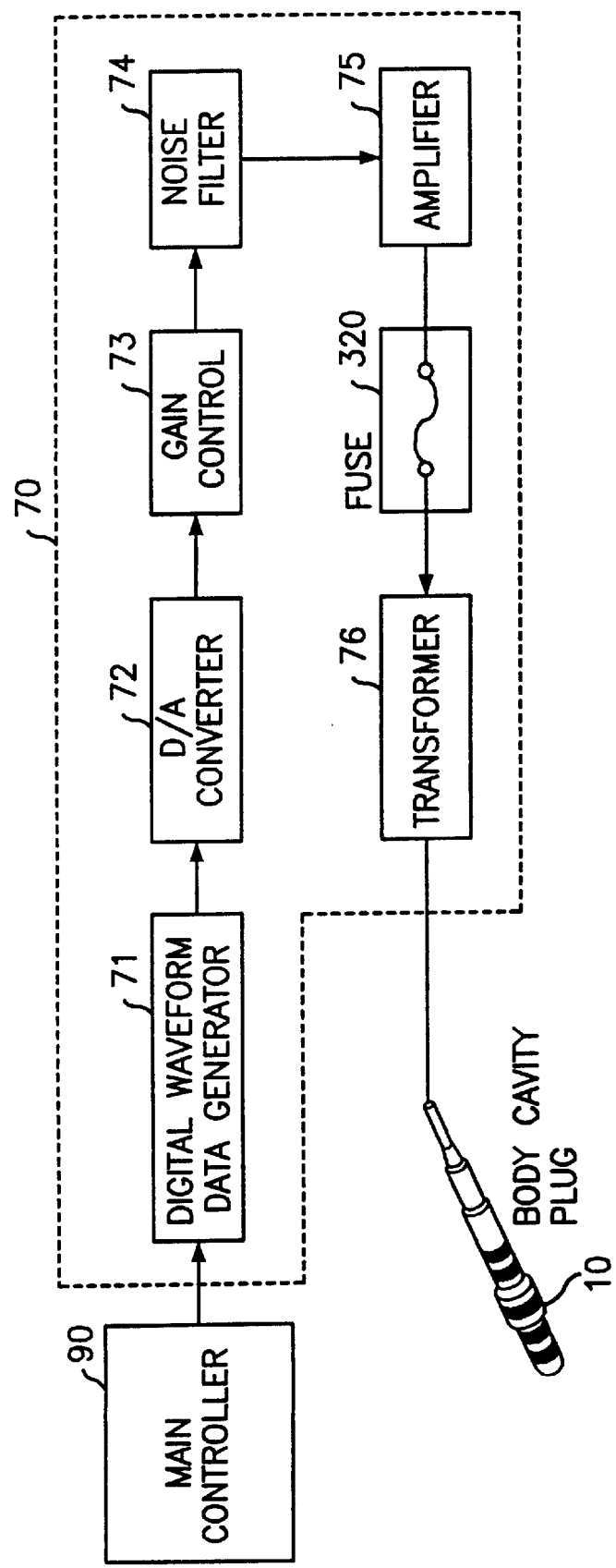

Referring to FIG. 12d, the safety circuit includes a fuse 320. In FIG. 12d, the same parts with those of FIG. 12a have the same reference numerals and the explanation thereof will be omitted.

Referring to FIG. 12d, there is a fuse 320 between the amplifier 75 and the transformer 76. The fuse 320 is configured to break when the output of the amplifier 75 exceeds a predetermined value. In a preferred embodiment, the above-mentioned fuse 320 can be made with a polymer switch which can be restored after resetting the power.

Referring to FIG. 12e, the stimulation signal generator 70 includes an over-current detector 332 and a switch 334 between the transformer 76 and the body-cavity plug, as a safety circuit. In FIG. 12e, the same parts with those of FIG. 12a have the same reference numerals and the explanation thereof will be omitted.

Referring to FIG. 12e, the over-current detector 332 detects when the output of the transformer 76 exceeds a predetermined current value to generate a bypass signal. When the switch 334 is turned on in response to the bypass signal, the output of the transformer 76 is not delivered to the body-cavity plug 10, but returns to the transformer 76 through the switch 334.

Therefore, it prevents over-current from being delivered to a human body through a body-cavity plug 10.

Figure 12F:
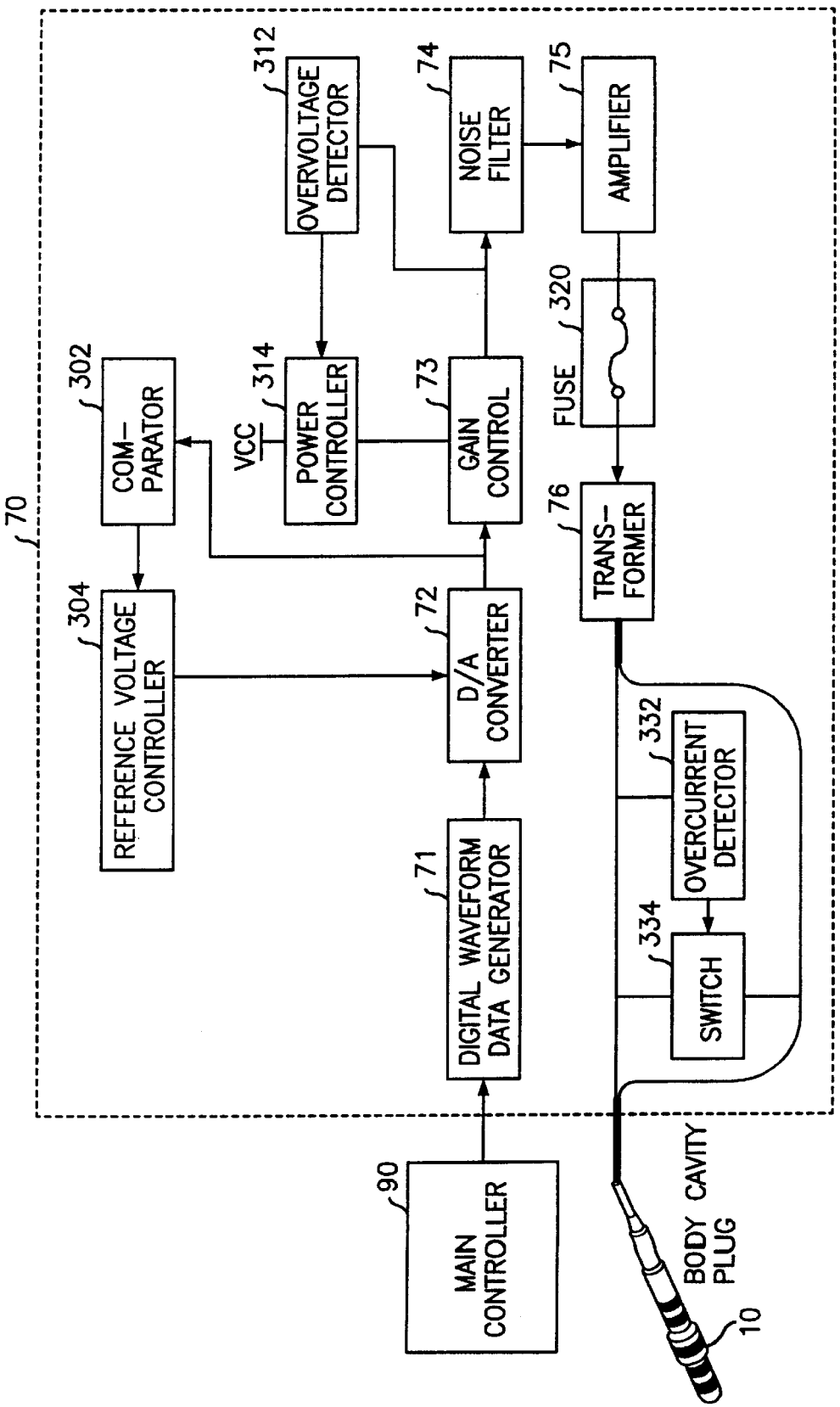

FIG. 12f is a block diagram illustrating a stimulation signal generator including such a safety circuit, and the explanation for each part is the same as above. As shown in the diagram, the stimulation signal generator 70 may include only one safety circuit, but for better protection, it is preferable to have at least 2 among said safety circuits. By constructing the stimulation signal generator 70 as above, it protects patients from the danger of excessive stimulation signals being delivered to their bodies.

Figure 13:
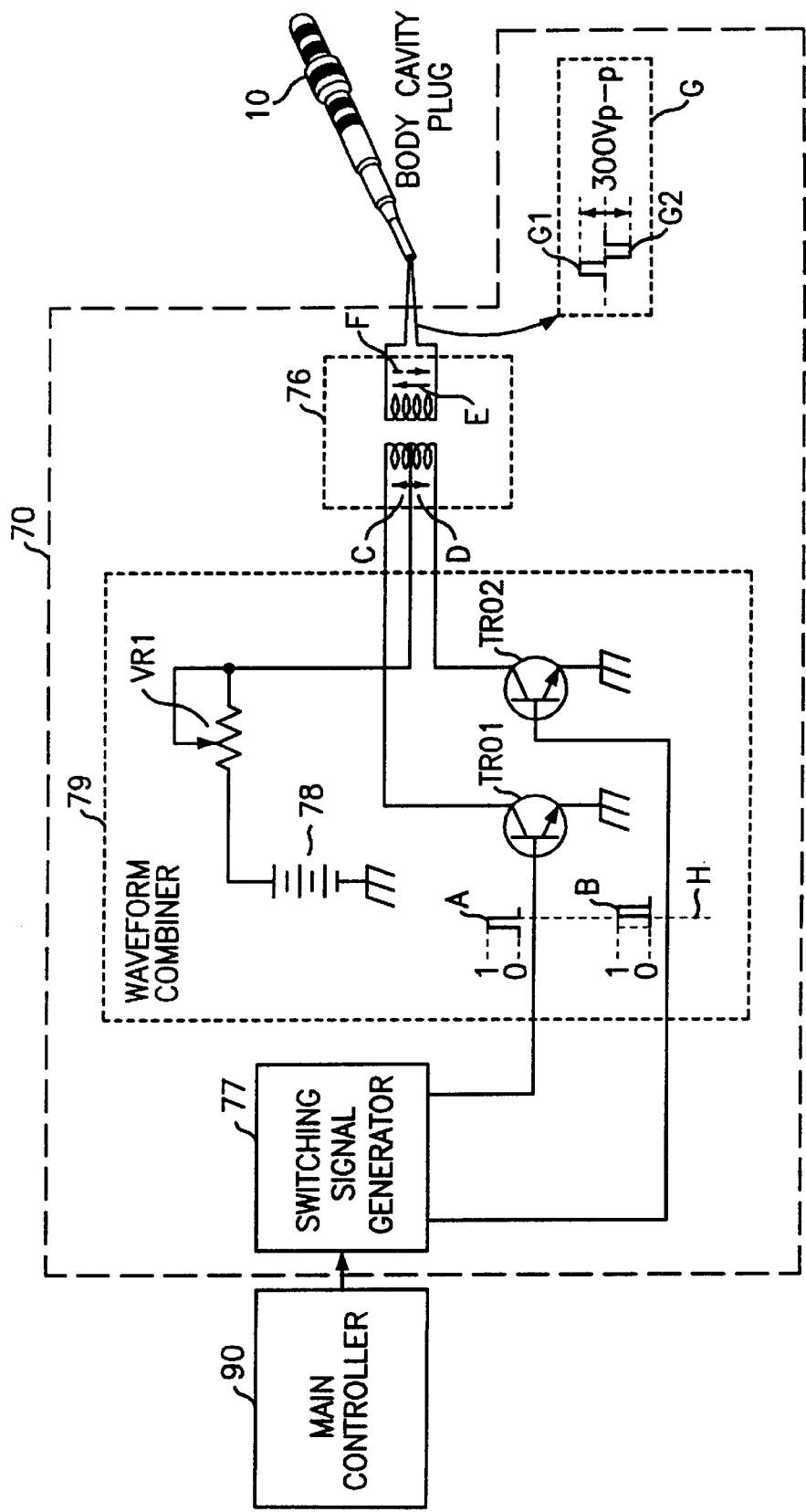
FIG. 13 is a detailed block diagram for illustrating another embodiment of the stimulation signal generator 70 shown in FIG. 7.

FIG. 13 is a detailed block diagram of another embodiment of the stimulation signal generator 70 shown in FIG. 7. The stimulation signal generator 70 of FIG. 13 comprises a switching signal generator 77, a waveform combiner 79 and a transformer 76. When the data on the stimulation signal S-SIG are applied from the main controller 90 to the switching signal generator 77, the switching signal generator 77 generates a plurality of switching signals that becomes alternatively activated according to the stimulation signal data.

In accordance with one example, the switching signal generator 77 can be implemented by a parallel I/O controller and/or a subsidiary controller. In this case, the output from the switching signal generator 77 becomes pulse signals that become activated alternatively. Such pulse signals are applied to the waveform combiner 79.

Specifically, the waveform combiner 79 includes transistors TR01 and TR02, a variable resistor VR1 and a DC battery 78. The first output A of the switching signal generator 77 is applied to the base of the transistor TR01, and the second output B to the base of the transistor TR02. The emitter of the transistor TR01 and the emitter of the transistor TR02 are grounded, and each collector is connected to the first and second input terminals of the transformer 76. In addition, the reference voltage according to the DC battery 78 and variable resistor VR1 is applied to the transformer 76. Here, the level of the reference voltage can be controlled by controlling the resistance value of the variable resistor VR1, and the resistance value control can be made either in an analog manner or in a digital manner.

The transistors TR01 and TR02 are alternately turned on and the first and second input terminals are electrically-coupled to the ground alternately. For example, when the transistor TR01 is turned on, the first input terminal of the transformer 76 is grounded and the first directional voltage C is applied to the primary coil of the transformer 76. Also, when the transistor TR02 is turned on, the second input terminal of the transformer 76 is grounded and the second directional voltage D is applied to the primary coil of the transformer 76. Here, the first directional voltage C has the opposite phase to that of the second directional voltage D, and the amplitudes of the first and second directional voltages C and D are the same as the reference voltage. Voltage E is induced to the secondary coil of the transformer 76 by the first directional voltage C, and voltage F is induced to the secondary coil of the transformer 76 by the second directional voltage D. Voltage E and voltage F are the opposite phase to each other and the amplitudes thereof are substantially the same. Thus the output of the transformer 76 is a biphasic pulse waveform G. The peak-to-peak voltage between the positive pulse G1 and the negative pulse G2 of the bi-phasic pulse waveform G is about 300V.

In addition, if the switching signal generator 77 is implemented by PIO, the output of the transformer 76 can be mono-phasic or bi-phasic signals depending on the output of PIO. This is the same for the switching signal generator 77 being implemented including a subsidiary controller.

Figure 14:
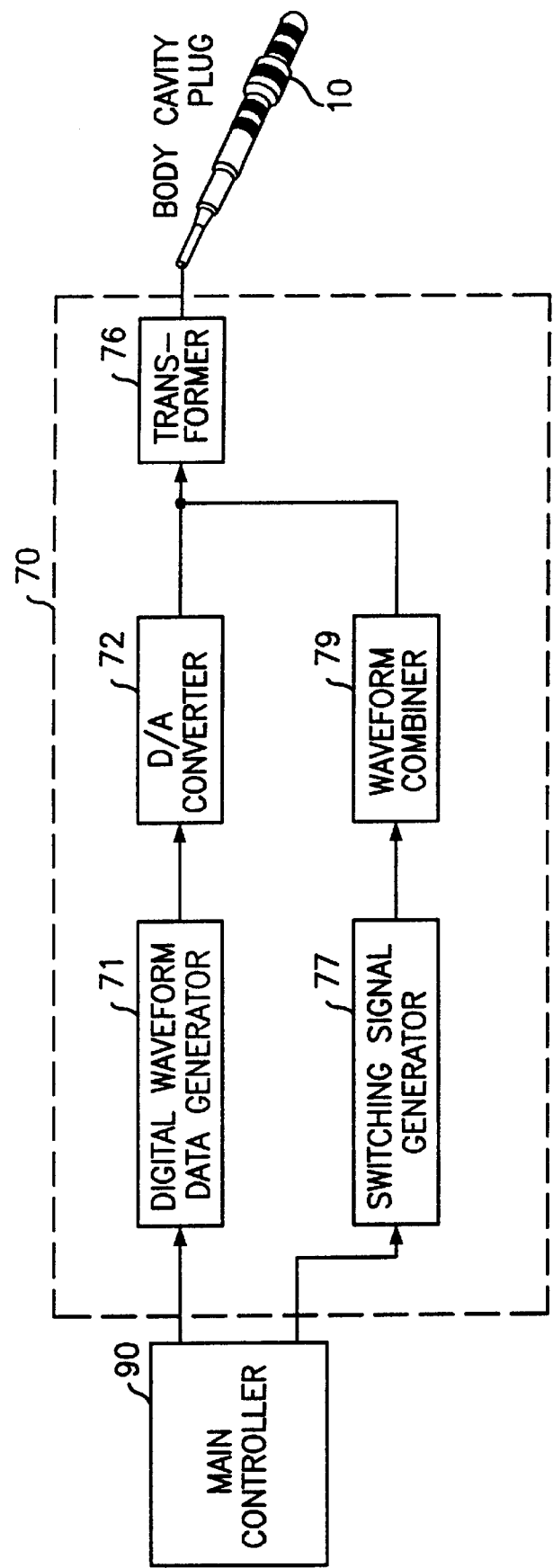
FIG. 14 is a detailed block diagram for illustrating yet another embodiment of the stimulation signal generator 70 shown in FIG. 7.

FIG. 14 is a detailed block diagram of still another embodiment of the stimulation signal generator 70 shown in FIG. 7 and FIG. 11. In FIG. 14, the same parts as in FIG. 12 and FIG. 13 have the same reference numerals with those of FIGS. 12 and 13, and the description thereof will be omitted.

Referring to FIG. 14, the stimulation signal generator 70 comprises a digital waveform data generator 71, a D/A converter 72, a transformer 76, a switching signal generator 77 and a waveform combiner 79. The switching signal generator 77 can be a parallel I/O control PIO and/or a subsidiary controller. The outputs of the D/A converter 72 and the waveform combiner 79 are wired-OR'ed and applied to the transformer 76. The output of the transformer 76 is applied to the electrode 10. In case of configuring the stimulation signal generator 70 as shown in FIG. 14, either the digital waveform data generator 71 and the D/A converter 72, or the switching signal generator 77 and the waveform combiner 79 are selectively activated.

Figure 15:
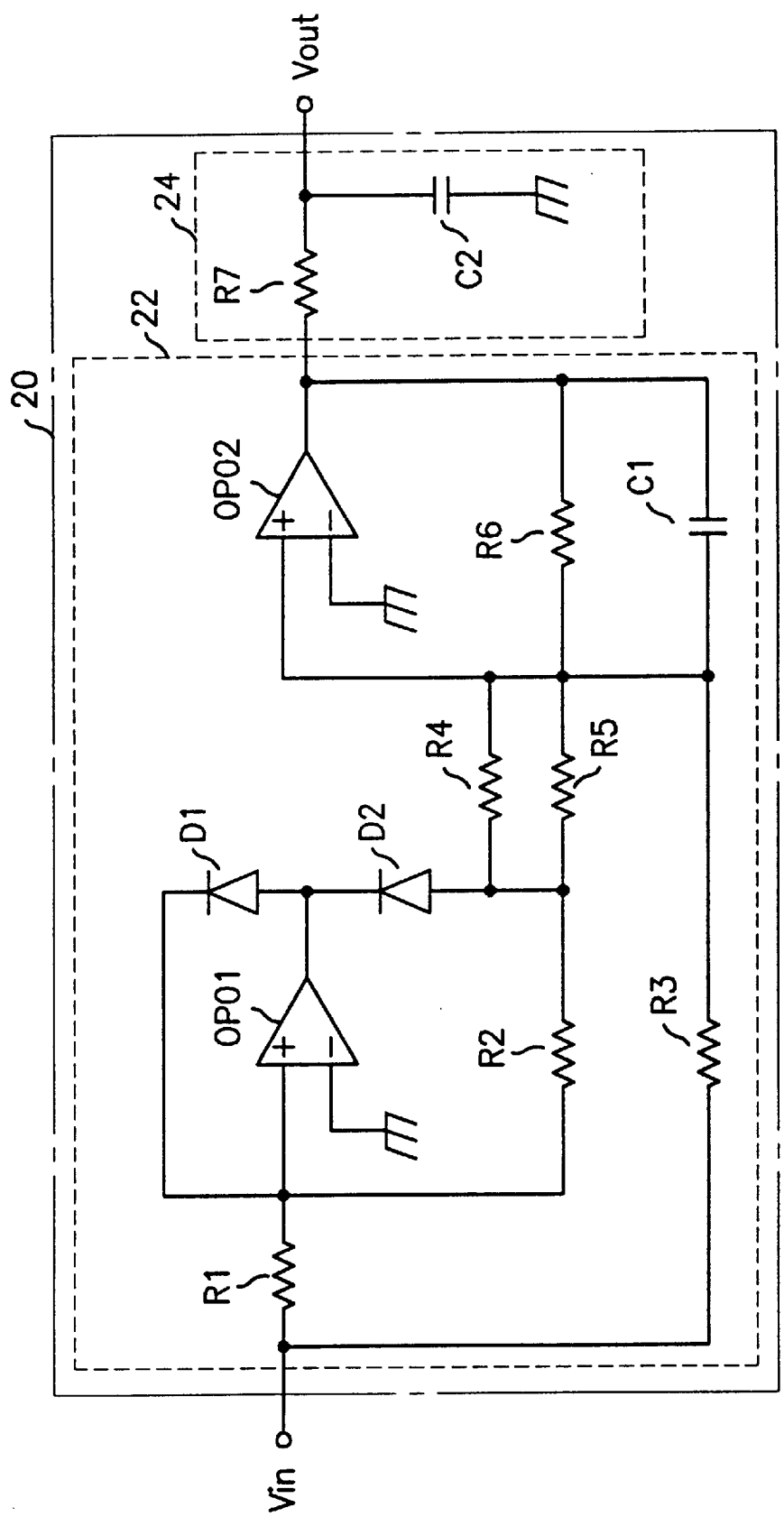
FIG. 15 is a detailed circuit diagram for illustrating the envelope detector 20 shown in FIGS. 5–11.

FIG. 15 is a circuit diagram of one preferred embodiment of the envelope detector 20 in FIGS. 5 to 11.

Referring to FIG. 15, the envelope detector 20 comprises a small-signal full wave rectifier 22 and a low-pass filter 24. The small-signal full wave rectifier 22 includes a plurality of resistors R1, R2, R3, R4, R5, a plurality of diodes D1, D2, a capacitor C1 and a plurality of differential amplifier OP01, OP02. The small-signal full wave rectifier rectifies the signal applied to the input terminal Vin of the envelope detector 20. In addition, the low-pass filter 24 comprises a resistor R6 and a capacitor C2, and performs a low-pass filtering on the output of the small-signal full rectifier 22 so as to produce the filtered-signal through the output terminal Vout of the envelope detector 20. At this time, the operation amplifiers OP01, OP02 of the small-signal full wave rectifier may be preferably implemented by Texas Instruments' TL072 and the diodes D1 and D2 may be implemented by IN4148. Also, the each resistance of R1, R2, R3, R4, R5, R6 is 100 k$\Omega$, and the resistance of R7 is 10 k$\Omega$, and the capacitor C1 and capacitor C2 can be ceramic capacitors of 102 pF and 103 pF, respectively.

Figure 16A:
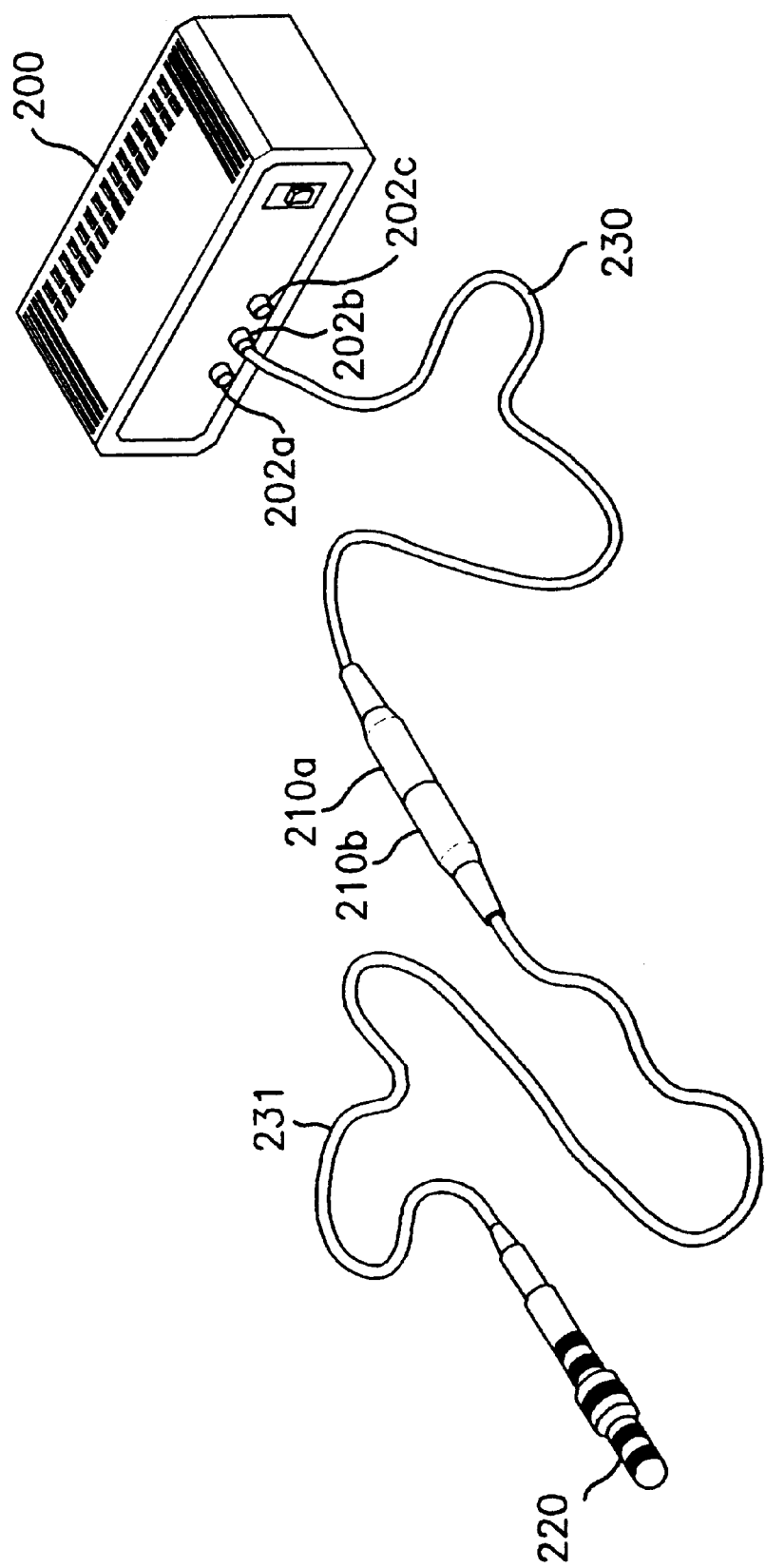
FIG. 16a and FIG. 16b are for illustrating the medical treatment apparatus according to another embodiment of the present invention.
Figure 16B:
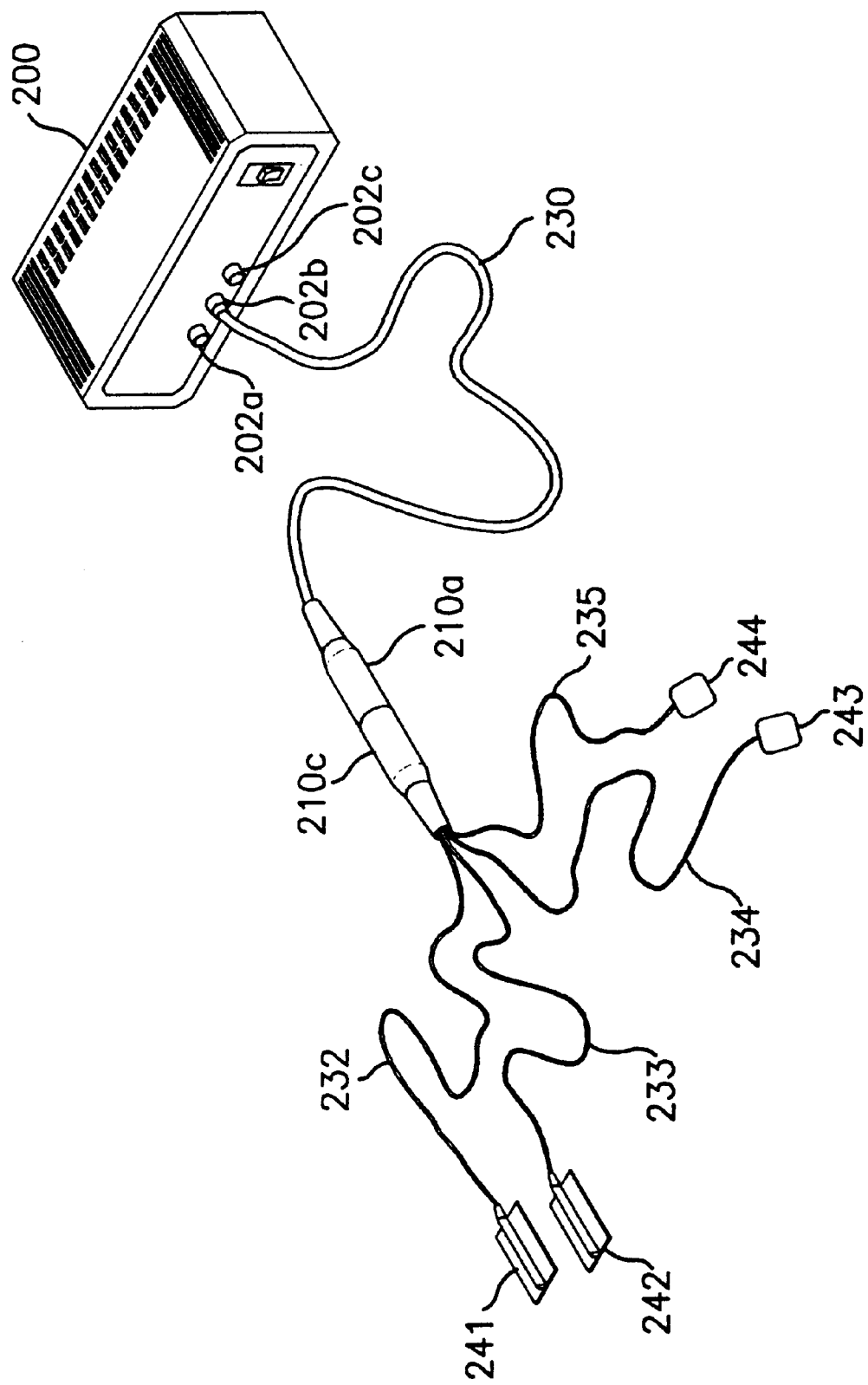

FIG. 16a and FIG. 16b are diagrams for illustrating still another preferred embodiment of the present invention.

Referring to FIG. 16a, the main body equipment 200 has a plurality of ports 202a, 202b and 202c. As described above, the main body equipment may comprise an EMG signal processor 80, a stimulation signal generator 70, a main controller 90, a memory 50, an operation unit 60 and a communication processor 100. In addition, the port 202b can be electrically coupled to the EMG signal processor and the stimulation signal generator. The port 202b is also coupled to a vaginal electrode 220 through a cable 230, universal connectors 210a, 210b, and a cable 231. At this time, the cable 230 and the universal connector 210a constitute the interfacing unit, and the universal connector 210b, the cable 231 and the electrode 220 constitute the electrode part. Thus for treatment of urinary incontinence, one should connect the universal connectors 210a and 210b together, and connect the cable 230 to the port 202b. The universal connectors 210a and 210b are formed so that they can be connected to each other.

Referring to FIG. 16b, the universal connector 210c, the cables 232, 233, 234, 235, and the pad-typed electrodes 241, 242, 243, 244 constitute one unit, and the universal connectors 210a and 210c may be combined together. The pad-type electrodes in FIG. 16b are adhesive and are contacted on the skin surface to which treatment, for example, low-frequency physical therapy, applies.

As shown in FIGS. 16a and 16b, various electrodes can be connected to the port 202b through the universal connector. Thus the main body equipment can be used not only for treatment of urinary incontinence, but also for treatment of constipation, fecal incontinence, low-frequency physical therapy, electrical treatment, electrical induction of ejaculation, medical biofeedback training, measurement of EMG, muscular stimulation, measurement of bladder impedance and bladder pressure and so on. Various electrodes can include vaginal electrode, rectal electrode, pad-type electrode for physical therapy and plug-type electrode for measurement of bladder impedance.

In addition, as shown in FIG. 16a and FIG. 16b, the ports 202a and 202c can be used for other purposes such as for connection to a monitor port or to other sensors.

Also, the main body equipment 200 in FIG. 16a and FIG. 16b is shown suitable for clinical use. Specifically, the main body equipment 200 in FIG. 16a and FIG. 16b can be coupled to a computer or other equipment through a connecting cable. If the device is used in connection with a computer, the main body equipment 200 does not need to include display unit 30, but it is possible to use a computer.

However, the main body equipment 200 is not limited to the appearance shown in FIG. 16a and FIG. 16b, but might have different appearances. For example, differently from the FIG. 16a and FIG. 16b, if the device should be designed portable for personal use at home, the main body equipment 200 can include the display unit 30. At this time, the display unit 30 can be implemented by an LCD panel.

Figure 17:
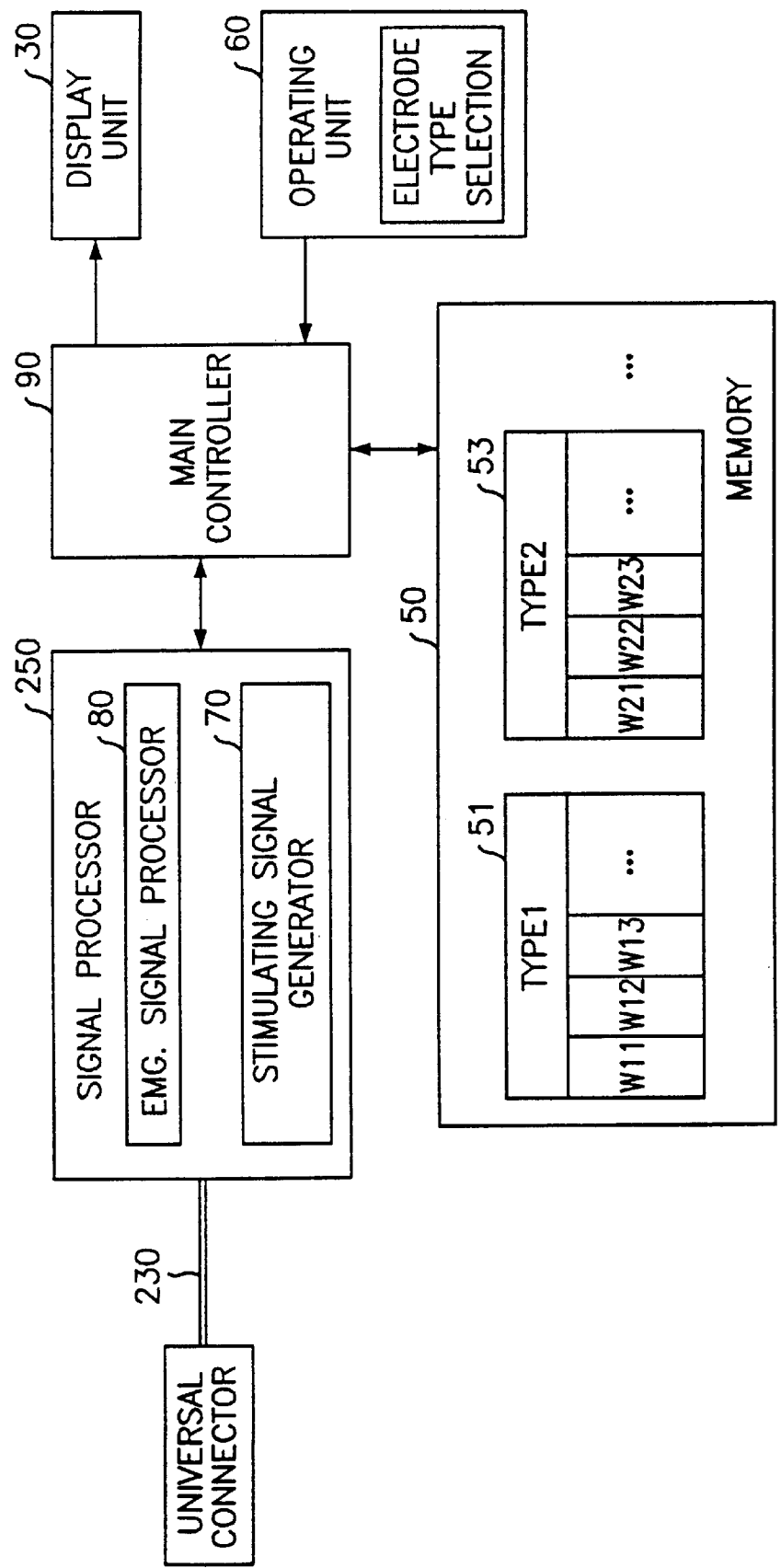
FIG. 17 illustrates a detailed block diagram of the main body equipment 200 shown in FIGS. 16a and 16b.

FIG. 17 is a detailed block diagram of one preferred embodiment of the main body equipment 200 in FIG. 16a and FIG. 16b. The main body equipment 200 comprises a signal processor 250, a main controller 90, a display unit 30, an operation unit 60 and a memory 50. The operation unit 60 can select the type of electrode to use, and the memory 50 has one or more stimulation signal waveforms for each electrode. For example, the data on stimulation signal waveforms W11, W12, W13, . . . for the vaginal electrode are stored in a domain called TYPE1, and the data on stimulation signal waveforms W21, W22, W23, . . . for the pad-type electrode are stored in a domain called TYPE2. If the vaginal electrode is selected by the operation unit 60, one of the data on the stimulation signal waveforms pertaining to TYPE1 is selectively applied to the stimulation signal generator 70 by the main controller 90. At this time, selecting one of the data on the stimulation signal waveforms in TYPE1 can be done based on the user's command or pre-programmed treatment training data. Therefore, the user can use one device for various purposes.

Figure 18:
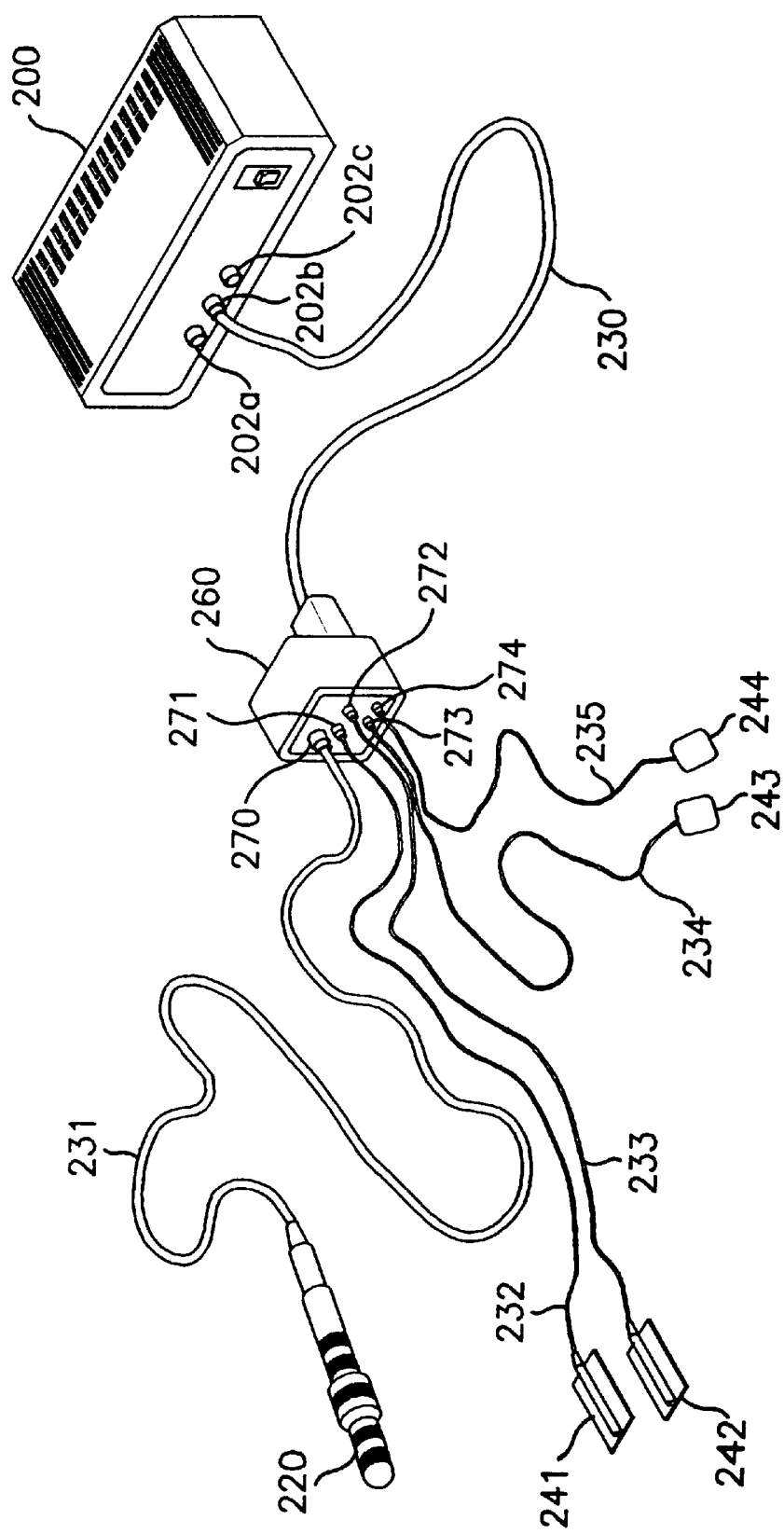
FIG. 18 shows the medical treatment apparatus according to yet another embodiment of the present invention.

FIG. 18 is a diagram for illustrating still another embodiment of the present invention. The universal connector 260 in FIG. 18 is differently shaped from that in FIG. 16. In addition, the universal connector 260 has a plurality of connecting ports 270, 271, 272, 273, 274, and each port has a different shape and/or size to prevent connection of the wrong plug. In this case, the users don't have to select the type of the electrode to be used by way of the operation unit 60, because the port being coupled to the electrode of choice is recognized according to the connecting ports 270, 271, 272, 273, and 274. At this time, an advantage lies in that malfunction of the device by connecting the wrong connector can be prevented. Also, even the operation unit 60 selects the right type of the electrode, no stimulation signal is generated when the electrode of choice does not match with the electrode actually connected. Thus the patient is protected from the malfunction of the device by the user's fault.

This protective mechanism against malfunction can also be embodied for the use of universal connectors shown in FIG. 16a and FIG. 16b. For example, each type of electrode can be assigned with an identification number, and when connected, the unique identification number can be applied to the main controller 90 through the cable, so that the malfunction of the equipment can be prevented.

As described so far, the present invention not only has a simple overall structure as an electrical treatment device by using EMG signal envelopes, but also displays information such as the status of the patient's muscular contraction and so on for easy visualization for the patient and the doctor. Since the small and lightweight of the overall apparatus can be made due to the simple structure, a portable urinary incontinence treatment apparatus can be easily made. Thus an advantage lies in that the patient can do, for example, light housework during treatment.

In addition, the electrical apparatus for medical treatment can be widely used by the universal connectors which enable connection of various types of electrode, and by storing waveform information corresponding to each type of electrode within the apparatus. Thus an advantage lies in that one can purchase a cost-effective device for various purposes.

Although the present invention has been described with reference to preferred embodiments, those skilled in the art will appreciate that changes may be made in form and detail without departing from the spirit and scope of the invention.

What is claimed is:

1. An apparatus for medical treatment comprising:

a main body equipment for generating a stimulation signal to be delivered to a patient's body and processing an EMG signal detected from the patient's body, said main body equipment having at least one port for receiving said stimulation signal and said EMG signal;

an interfacing connection part; and a plurality of electrode parts for delivering said stimulation signal and detecting said EMG signal, wherein said interfacing connection part includes a first cable having one end capable of being connected to the port of said main body equipment, and a first type of universal connector formed on the other end of said first cable; and each of said plurality of electrode parts comprises one or more electrodes adapted to be inserted into a body cavity or to be contacted with a body part, a second cable having one end capable of being connected to said electrodes, and a second type of universal connector on the other end of said second cable to be connected to said first type of universal connector.

2. The apparatus for medical treatment according to claim 1, wherein said plurality of electrodes includes an electrode adapted to be inserted into a vagina.

3. The apparatus for medical treatment according to claim 2, wherein said plurality of electrodes includes a pad type electrode.

4. The apparatus for medical treatment according to claim 1, wherein said main body equipment comprises:

an operation unit for selecting at least one of said plurality of electrodes to use; and if the first type of universal connector is coupled to the second type of universal connector, means for determining whether the coupled second type of universal connector belongs to an electrode selected by the operation unit.

5. The apparatus for medical treatment according to claim 1, wherein the main body equipment comprises:

an EMG signal processor including an envelope detector for detecting an envelope from the EMG signal detected from the electrode and for producing the EMG envelope signal, so as to process the EMG signal;

a display unit for displaying information on medical treatment based on the EMG envelope signal;

an operation unit for inputting a user's command including an electrode selection command which indicates which electrode is to be used;

a memory for storing information related to the medical treatment including information on a plurality of training goal waveforms each of which corresponds to said plurality of electrodes, respectively;

a stimulation signal generator for generating the stimulation signal based on one of the training goal waveforms which are applied from the memory or the operation unit, so as to apply the stimulation signal to the electrode through the interface connection part; and a main controller for controlling said display unit, said operation unit, said memory, said EMG signal processor and said stimulation signal generator.

* * * * *